(12) United States Patent
Shigeta

(10) Patent No.: US 11,399,751 B2
(45) Date of Patent: Aug. 2, 2022

(54) ENDOSCOPE SYSTEM AND METHOD OF OPERATING ENDOSCOPE SYSTEM

(71) Applicant: FUJIFILM Corporation, Tokyo (JP)

(72) Inventor: Norimasa Shigeta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 852 days.

(21) Appl. No.: 15/993,599

(22) Filed: May 31, 2018

(65) Prior Publication Data

US 2018/0271412 A1 Sep. 27, 2018

Related U.S. Application Data

(63) Continuation of application No. PCT/JP2016/086341, filed on Dec. 7, 2016.

(30) Foreign Application Priority Data

Dec. 22, 2015 (JP) .............................. JP2015-250538

(51) Int. Cl.
*A61B 5/1459* (2006.01)
*A61B 1/06* (2006.01)
(Continued)

(52) U.S. Cl.
CPC ........ *A61B 5/1459* (2013.01); *A61B 1/00009* (2013.01); *A61B 1/00197* (2013.01);
(Continued)

(58) Field of Classification Search
CPC . A61B 5/1455; A61B 5/14551; A61B 5/1459; A61B 5/14552; A61B 1/00009;
(Continued)

(56) References Cited

U.S. PATENT DOCUMENTS

| 2008/0260218 A1* | 10/2008 | Smith | A61B 5/444 |
| | | | 382/128 |
| 2011/0077462 A1* | 3/2011 | Saitou | A61B 1/063 |
| | | | 600/109 |

(Continued)

FOREIGN PATENT DOCUMENTS

| EP | 2550910 | 1/2013 |
| EP | 3278710 | 2/2018 |

(Continued)

OTHER PUBLICATIONS

Color Mixing (www.webexhibits.org/causesofcolor/1BA.html, retrieved Aug. 20, 2021).*

(Continued)

*Primary Examiner* — Carolyn A Pehlke
(74) *Attorney, Agent, or Firm* — JCIPRNET

(57) ABSTRACT

The endoscope system (10) includes a light source unit (20) that emits correction illumination light to be used for the correction in the correction mode in which the biological information observation mode is corrected and emits white light at least once; a compensation amount calculation unit (76) that calculates a compensation amount of data to be used in the biological information observation mode using correction images obtained using the correction illumination light; a correction unit (77) that corrects the biological information observation mode by compensating for the data using the compensation amount; and a display control unit (66) that displays a white light image, which is obtained by imaging the observation object using the white light, on a display unit in the correction mode.

16 Claims, 20 Drawing Sheets

(51) Int. Cl.
*A61B 1/00* (2006.01)
*A61B 5/1455* (2006.01)
*G02B 23/24* (2006.01)
*A61B 1/04* (2006.01)

(52) U.S. Cl.
CPC .......... *A61B 1/0638* (2013.01); *A61B 1/0646* (2013.01); *A61B 1/0684* (2013.01); *A61B 5/14552* (2013.01); *G02B 23/2469* (2013.01); *A61B 1/00188* (2013.01); *A61B 1/041* (2013.01)

(58) Field of Classification Search
CPC ............ A61B 1/00057; A61B 1/00163; A61B 1/00165; A61B 1/06; A61B 1/04; A61B 1/0188; A61B 1/0646; A61B 1/0653; A61B 1/0661; A61B 1/0684; G06T 7/0012; G06T 7/20; G06T 7/30; G06T 7/90; H04N 13/246; H04N 13/257
See application file for complete search history.

(56) References Cited

U.S. PATENT DOCUMENTS

| | | | |
|---|---|---|---|
| 2012/0053434 A1* | 3/2012 | Saito | A61B 1/063 600/324 |
| 2012/0218394 A1 | 8/2012 | Yoshino et al. | |
| 2013/0030268 A1 | 1/2013 | Saito | |
| 2013/0278738 A1* | 10/2013 | Hayashi | A61B 1/00006 348/68 |
| 2014/0210975 A1* | 7/2014 | Hirakawa | G02B 23/26 348/68 |
| 2016/0183774 A1 | 6/2016 | Shiraishi | |
| 2017/0135555 A1* | 5/2017 | Yoshizaki | A61B 1/0002 |
| 2017/0243325 A1* | 8/2017 | Sasaki | A61B 1/0638 |
| 2017/0272720 A1* | 9/2017 | Oki | H04N 9/73 |

FOREIGN PATENT DOCUMENTS

| | | |
|---|---|---|
| EP | 3369361 | 9/2018 |
| JP | 2006341025 | 12/2006 |
| JP | 2011104011 | 6/2011 |
| JP | 2013022341 | 2/2013 |
| JP | 2013215471 | 10/2013 |
| WO | 2015045703 | 4/2015 |
| WO | 2015064436 | 5/2015 |

OTHER PUBLICATIONS

"International Search Report (Form PCT/ISA/210) of PCT/JP2016/086341," dated Mar. 7, 2017, with English translation thereof, pp. 1-3.

"Written Opinion of the International Searching Authority (Form PCT/ISA/237) of PCT/JP2016/086341," dated Mar. 7, 2017, with English translation thereof, pp. 1-7.

"Search Report of Europe Counterpart Application", dated Dec. 12, 2018, p. 1-p. 10.

"Office Action of Europe Counterpart Application", dated Feb. 18, 2021, p. 1-p. 5.

* cited by examiner

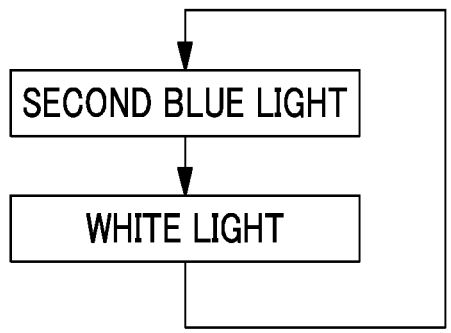
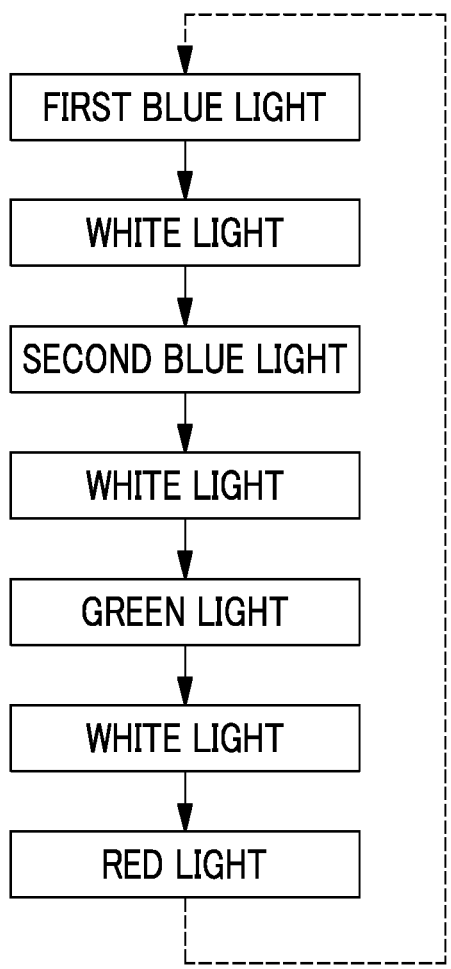

ENDOSCOPE SYSTEM AND METHOD OF OPERATING ENDOSCOPE SYSTEM

CROSS-REFERENCE TO RELATED APPLICATIONS

This application is a Continuation of PCT International Application No. PCT/JP2016/086341 filed on Dec. 7, 2016, which claims priority under 35 U.S.C. § 119(a) to Japanese Patent Application No. 2015-250538 filed on Dec. 22, 2015. Each of the above application(s) is hereby expressly incorporated by reference, in its entirety, into the present application.

BACKGROUND OF THE INVENTION

1. Field of the Invention

The present invention relates to an endoscope system that calculates biological information on an observation object, and a method of operating the endoscope system.

2. Description of the Related Art

In the medical field, it is general to perform diagnosis using endoscope systems including a light source device, an endoscope, and a processor device. Particularly, endoscope systems, which not only image an observation object but also obtain observation images in which specific tissues or structures, such as blood vessels and duct structures, are enhanced, have become widespread. In such endoscope systems, for example, the wavelength of illumination light to be radiated to the observation object is studied, or estimation processing is performed on images obtained by imaging the observation object. As a result, the observation images in which the specific tissues and structures are enhanced are obtained.

Additionally, in recent years, there are also endoscope systems for obtaining biological information on the basis of images obtained by imaging the observation object. For example, diagnosis of a lesion location using the oxygen saturation (biological information) of hemoglobin in blood is being performed. As a method of calculating the oxygen saturation, for example, as described in JP2013-022341A (JP5426620B), there is a method of acquiring image obtained by radiating light in a wavelength range where the light absorption coefficients of oxygenated hemoglobin and reduced hemoglobin are different from each other to an observation object, calculating predetermined arithmetic values using a plurality of images (hereinafter referred to as mainly captured images) include at least this image, and calculating oxygen saturation using a correlation in which the arithmetic values are matched with the oxygen saturation.

There is a case where the correlation between the arithmetic values and the oxygen saturation as described above varies due to differences in various parts, such as the esophagus, the stomach, or the large intestine, or differences in patients, such as men and women or adults and children. In contrast, in JP2013-022341A (JP5426620B), before actually observing the inside of the body using the oxygen saturation, the oxygen saturation of a normal part is calculated by imaging (hereinafter referred to as preliminary capturing) the normal part of a patient and a part and obtaining a plurality of images (hereinafter referred to as preliminarily captured images). Then, a difference between the oxygen saturation of an actual normal part of the patient and the part and a reference value (for example, 70%) of the oxygen saturation of a general normal part in which the correlation is determined is calculated, and the correlation is compensated for on the basis of the calculated difference. Accordingly, in JP2013-022341A (JP5426620B), the oxygen saturation is calculated so that the oxygen saturation can be accurately calculated irrespective of parts, patient's individual differences, or the like, and an observation mode (hereinafter referred to as an oxygen saturation observation mode) in which an image showing the value of the oxygen saturation is generated and displayed is corrected.

In addition, there is known an endoscope system that in which a white light image obtained using white light and a special light image obtained using special light, such as so-called narrowband light or fluorescence, are alternately acquired, and an attention region obtained by processing the special light image is enhanced and displayed on the white light image (JP2011-104011A).

SUMMARY OF THE INVENTION

In order to obtain the plurality of mainly captured images to be used for the calculation of the oxygen saturation in the oxygen saturation observation mode, it is necessary to change the wavelength or the like of the illumination light to image the observation object two or more times. In a case where there is any movement in the observation object between these kinds of imaging, the calculation accuracy of the oxygen saturation decreases due to the positional deviation of the observation object between the respective mainly captured images. For this reason, basically, it is preferable that the mainly captured images are continuously acquired in a short period of time as much as possible so as to be regarded to be all substantially simultaneously obtained.

Since a plurality of preliminarily captured images are required also in a case where the oxygen saturation observation mode is corrected, the accuracy of the correction decreases in a case where there is any movement in the observation object while the plurality of preliminarily captured images are captured. For this reason, similarly to the mainly captured images, basically, it is preferable to obtain a plurality of preliminarily captured images while there is no movement of the observation object. Particularly, in a case where the correction is inaccurate, the oxygen saturation that is calculated afterward becomes all inaccurate. Thus, it is more important to accurately correct the oxygen saturation observation mode accurately than keeping the calculation accuracy of the oxygen saturation from decreasing.

In the case of JP2013-022341A (JP5426620B), by correcting the oxygen saturation observation mode, the oxygen saturation can be calculated more accurately than in an endoscope system that does not correct the oxygen saturation observation mode. However, JP2013-022341A (JP5426620B) does not mention correction accuracy. Additionally, in JP2011-104011A, the white light image and the special light image are alternately obtained. However, there is no oxygen saturation observation mode. Thus, although natural, JP2011-104011A also does not mention the correction of the oxygen saturation observation mode.

Additionally, in JP2013-022341A (JP5426620B), the oxygen saturation that is one item of the biological information is observed. However, the same applies to a case where other biological information observation modes in which biological information other than the oxygen saturation is calculated by using a plurality of mainly captured images. That is, similarly to the above, it is necessary to acquire the plurality of preliminarily captured images while there is no movement of the observation object, to accurately correct the biological information observation mode.

An object of the invention is to provide an endoscope system capable of correcting a biological information observation mode more reliably and accurately than in the related art and a method of operating the endoscope system, in the endoscope system having the biological information observation mode and a correction mode that corrects the biological information observation mode.

The endoscope system of the present inventing is an endoscope system having a biological information observation mode in which biological information on an observation object is observed, and a correction mode in which the biological information observation mode is corrected. The endoscope system comprises a light source unit that emits correction illumination light to be used for a correction in the correction mode and emits white light at least once; a compensation amount calculation unit that calculates a compensation amount of data to be used in the biological information observation mode using correction images obtained by imaging the observation object using the correction illumination light; a correction unit that corrects the biological information observation mode by compensating for the data using the compensation amount; and a display control unit that displays a white light image, which is obtained by imaging the observation object using the white light, on a display unit in the correction mode.

It is preferable that the biological information is an oxygen saturation of the observation object.

It is preferable that the endoscope system further comprises a region setting unit that sets a portion of each of the correction images to a region to be used for the correction of the biological information observation mode, and the display control unit overlappingly displays the region set by the region setting unit on the white light image.

In the correction mode, it is preferable that the plurality of correction images are acquired, and a plurality of the white light images are acquired.

It is preferable that the endoscope system further comprises a light quantity ratio calculation unit that calculates a light quantity ratio of the plurality of white light images; and a light quantity ratio compensation unit that compensates for a light quantity ratio of the plurality of correction images using the light quantity ratio calculated by the light quantity ratio calculation unit.

It is preferable that the endoscope system further comprises a movement amount calculation unit that calculates a movement amount of the observation object; and a positional deviation compensation unit that compensates a positional deviation of the plurality of correction images using the movement amount.

It is preferable that the compensation amount calculation unit calculates a plurality of the compensation amounts by using some correction images among the plurality of correction images and changing a combination of the correction images to be used, and the correction unit compensates for the data to be used in the biological information observation mode using the plurality of compensation amounts or one of the plurality of compensation amounts.

It is preferable that the endoscope system further comprises a movement amount calculation unit that calculates a movement amount of the observation object, and the correction unit compensates for the data to be used in the biological information observation mode using a value obtained by weighting and averaging the plurality of compensation amounts using the movement amount.

It is preferable that the endoscope system further comprises a movement amount calculation unit that calculates a movement amount of the observation object, and the correction unit compensates for the data to be used in the biological information observation mode using one compensation amount selected from the plurality of compensation amounts using the movement amount.

That is, it is preferable that the light source unit makes a light emission interval of two correction illumination lights of a combination that most contributes to calculation accuracy of the compensation amount among a plurality of the correction illumination lights shorter than a light emission interval of the other correction illumination lights.

The method of operating an endoscope system of the invention is a method of operating an endoscope system having a biological information observation mode in which biological information on an observation object is observed, and a correction mode in which the biological information observation mode is corrected. The method comprises a step in which a light source unit emits correction illumination light to be used for a correction in the correction mode and emits white light at least once; a step in which a compensation amount calculation unit calculates a compensation amount of data to be used in the biological information observation mode using correction images obtained by imaging the observation object using the correction illumination light; a step in which a correction unit corrects the biological information observation mode by compensating for the data using the compensation amount; and a step in which a display control unit displays a white light image, which is obtained by imaging the observation object using the white light, on a display unit in the correction mode.

In the endoscope system and the method of operating an endoscope system of the invention, in the correction mode, not only the correction images are acquired, but also the white light images are acquired and displayed. For this reason, a situation where the correction cannot be accurately performed, such as a case where there is any movement in the observation object or a case where a portion unsuitable for the correction is imaged, while the plurality of correction images are acquired, can be easily perceived, the correction images can be acquired, and the correction can be performed again. For this reason, in the endoscope system and the method of operating the endoscope system of the invention, the biological information observation mode can be corrected more reliably and accurately than in the related art.

BRIEF DESCRIPTION OF THE DRAWINGS

FIG. 3 is a light emission pattern in an oxygen saturation observation mode (biological information observation mode).

FIG. 4 is a light emission pattern in a correction mode.

DESCRIPTION OF THE PREFERRED EMBODIMENTS

First Embodiment

Figure 1:
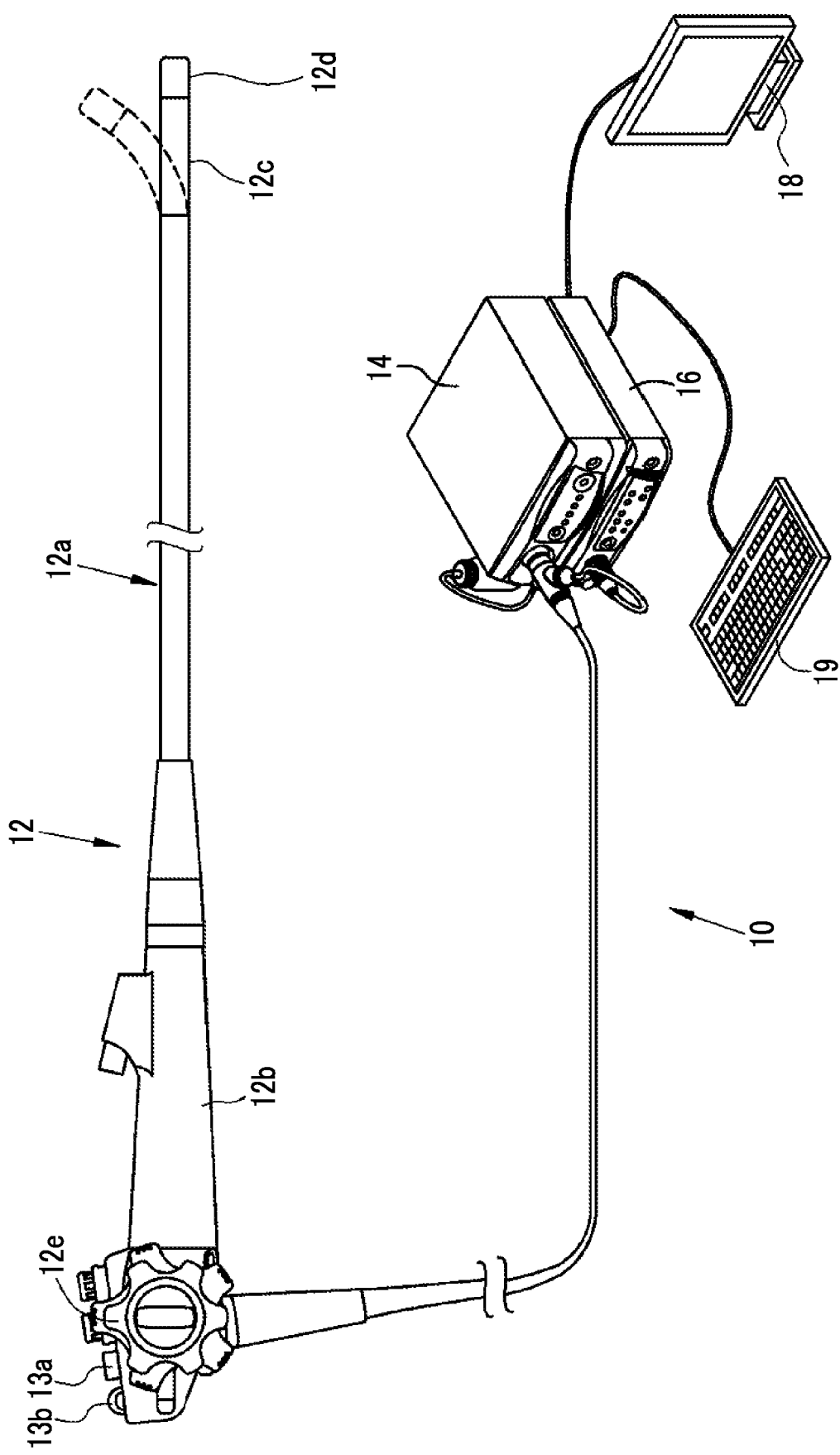
FIG. 1 is an external view of an endoscope system.

As illustrated in FIG. 1, an endoscope system 10 has an endoscope 12, a light source device 14, a processor device 16, a monitor 18 that is a display unit, and a console 19. The endoscope 12 is optically connected to the light source device 14 and is electrically connected to the processor device 16. The endoscope 12 has an insertion part 12a to be inserted into a subject, an operating part 12b provided at a base end portion of the insertion part 12a, and a bending part 12c and a distal end part 12d provided on a distal end side of the insertion part 12a. By operating an angle knob 12e of the operating part 12b, the bending part 12c is bent. The distal end part 12d is directed in a desired direction as a result of the bending of the bending part 12c. In addition, the distal end part 12d is provided with a jet port (not illustrated) that jets air, water, or the like toward an observation object.

Additionally, the operating part 12b is provided with a mode changeover switch 13a and a zooming operation part 13b other than the angle knob 12e. The mode changeover switch 13a is used for switching the operation of observation modes. The endoscope system 10 has a normal observation mode and a special observation mode. The normal observation mode is an observation mode in which a natural-tone image (hereinafter, referred to as a normal image) obtained by imaging the observation object using white light for illumination light is displayed on the monitor 18.

The special observation mode includes a biological information observation mode and a correction mode. The biological information observation mode is an observation mode in which biological information on the observation object is observed (the observation object is observed in a state where at least the biological information can be observed). The biological information is, for example, numerical information, such as oxygen saturation and the concentration of blood vessels, image information, which is a result obtained by extracting some tissue or the like from observable tissue or the like, such as "an image of blood vessels at a specific depth", and the like. In the present embodiment, the biological information observation mode is an oxygen saturation observation mode in which the oxygen saturation of the observation object is calculated. Therefore, in the oxygen saturation observation mode, the oxygen saturation of the observation object is calculated using a plurality of mainly captured images obtained by imaging the observation object, an image (hereinafter referred to as an oxygen saturation image) showing the values of the calculated oxygen saturation using pseudo-colors is generated, and the generated image is displayed on the monitor 18. The oxygen saturation image is an example of a biological information image, and a biological information image regarding the biological information to be calculated is generated and displayed in a case where other biological information is calculated, extracted, and the like (hereinafter referred to as calculation and the like) in the biological information observation mode.

The correction mode is a mode in which the biological information observation mode is corrected. The correction mode is automatically performed before the biological information is calculated and the like at least in the biological information observation mode. Additionally, in the correction mode, a normal part with no clear lesion or the like is preliminarily captured, and a compensation amount of data to be used for the calculation and the like of the biological information using preliminarily captured images obtained in the preliminary capturing is calculated. Then, by compensating for the data to be used for the calculation and the like of the biological information using the calculated compensation amount, the biological information observation mode is corrected.

That is, since the biological information observation mode is the oxygen saturation observation mode, the oxygen saturation observation mode is corrected in the correction mode. That is, in the correction mode, a compensation amount ΔD of the data to be used for the calculation of the oxygen saturation in the oxygen saturation observation mode is calculated using the preliminarily captured images. Then, the data to be used for the calculation of the oxygen saturation is compensated for using the calculated compensation amount ΔD. The data to be used for the calculation of the oxygen saturation is, for example, a correlation in which arithmetic values calculated using the plurality of mainly captured images, and the oxygen saturation are matched with each other. In addition, the correction mode can be executed at a certain timing during the biological information observation mode by operation input from the console 19 or the like. That is, during the execution of the biological information observation mode, the correction mode can be randomly interrupted and executed as needed.

The processor device 16 is electrically connected to the monitor 18 and the console 19. The monitor 18 outputs and displays the images in the respective observation modes, the image information accompanying the images, and the like. The console 19 functions as a user interface that receives input operation, such as function setting. In addition, an external recording unit (not illustrated) that records the images, the image information, and the like may be connected to the processor device 16.

Figure 2:
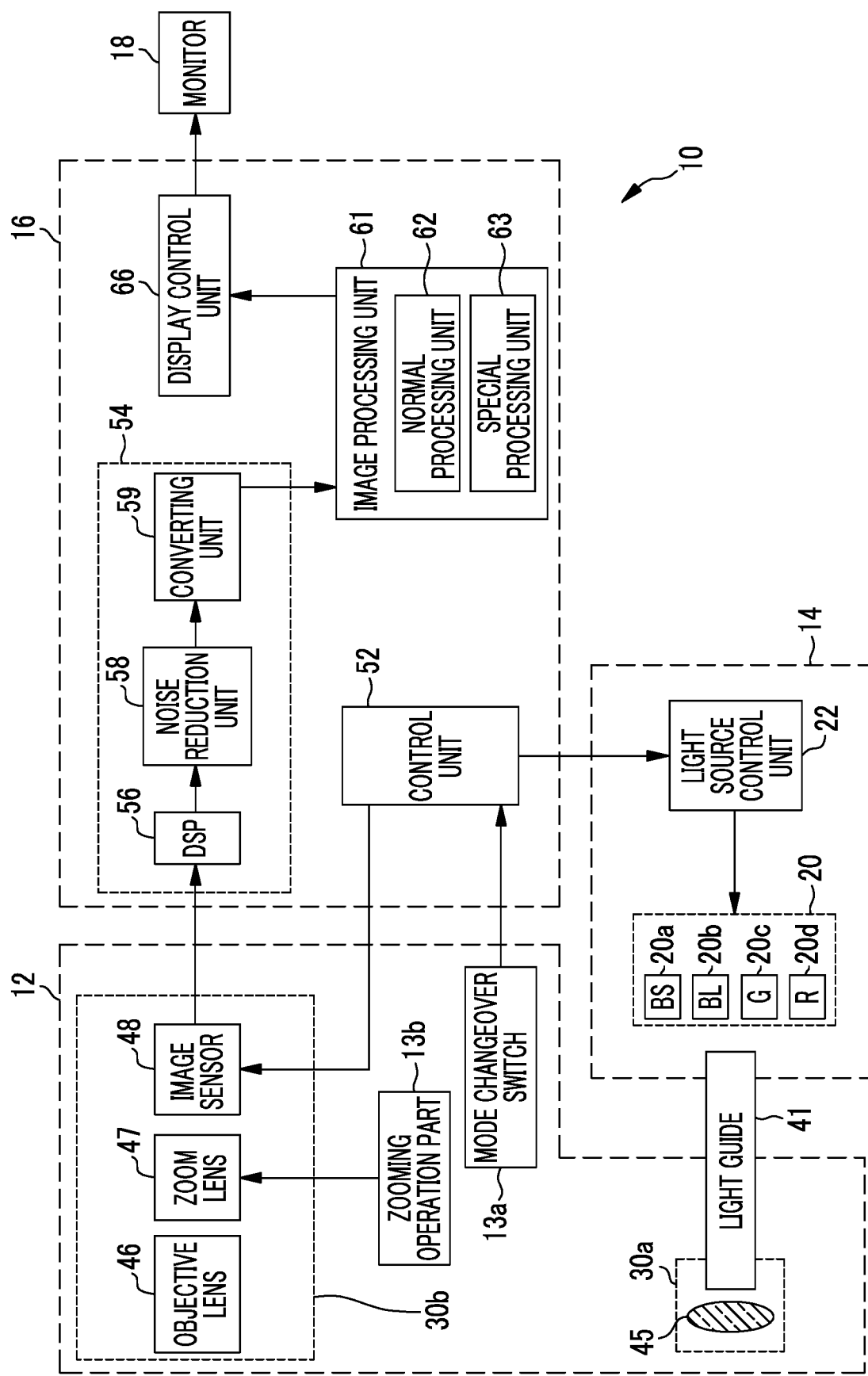
FIG. 2 is a block diagram of the endoscope system.

As illustrated in FIG. 2, the light source device 14 includes a light source unit 20 that emits the illumination light, and a light source control unit 22 that controls driving of the light source unit 20.

The light source unit 20 includes four light sources of a BS light source 20a, a BL light source 20b, a G light source 20c, and a R light source 20d. In the present embodiment, the BS light source 20a, the BL light source 20b, the G light source 20c, and the R light source 20d are all light emitting diodes (LEDs). Instead of such LEDs, a combination of a laser diode (LD), a fluorescent body, and a band limiting filter, a combination of a lamp, such as a xenon lamp, and a band limiting filter, or the like can be used for the light source unit 20.

The BS light source 20a is a blue light source that emits first blue light BS having a central wavelength of about 450±10 nm and having a wavelength range of about 420 nm to 500 nm. The BL light source 20b is a blue light source that emits blue, so-called narrowband light (hereinafter referred to as second blue light BL) having a central wavelength and a wavelength range of about 470 nm±10 nm. The G light source 20c is a green light source that emits green light G having a central wavelength of about 540±20 nm and having a wavelength range of about 480 nm to 600 nm. The R light source 20d is a red light source that emits red light R having a central wavelength of about 640±20 nm and having a wavelength range of about 600 nm to 650 nm.

The light source control unit 22 independently controls the timing of turning on/off the respective light sources 20a to 20d that constitute the light source unit 20, the light emission amount thereof at the time of the turn-on, and the like. Under the control of the light source control unit 22, the light source unit 20 emits normal observation illumination light to be used in the normal observation mode, biological information observation illumination light to be used in the biological information observation mode of the special observation mode, and correction illumination light to be used in the correction mode. That is, since the biological information observation mode is the oxygen saturation observation mode, the biological information observation illumination light is oxygen saturation observation illumination light.

In the case of the normal observation mode, the light source control unit 22 simultaneously turns on the BS light source 20a, the G light source 20c, and the R light source 20d. For this reason, the normal observation illumination light is white light including the first blue light BS, the green light G, and the red light R. In the present embodiment, in the case of the normal observation mode, the light source unit 20 always emits the above white light, but may emit the white light in accordance with imaging timings (hereinafter referred to as imaging frames) of the observation object.

In the case of the oxygen saturation observation mode, the light source control unit 22 alternately repeats turn-on or turn-off of the respective light sources 20a to 20d in a first pattern and a second pattern. The first pattern is a light emission pattern in which the BL light source 20b is independently turned on. For this reason, in the case of the first pattern, the second blue light BL becomes the illumination light. Meanwhile, the second pattern is a pattern in which the BS light source 20a, the G light source 20c, and the R light source 20d are simultaneously turned on. For this reason, in the case of the second pattern, the white light including the first blue light BS, the green light G, and the red light R becomes the illumination light. Hence, in the oxygen saturation observation mode, as illustrated in FIG. 3, the second blue light BL and the white light are alternately and repeatedly emitted in accordance with the imaging frames.

A mainly captured image obtained by imaging the observation object using the second blue light BL that is the illumination light of the first pattern, directly carries the most information on the oxygen saturation in a case where the observation object is irradiated. Meanwhile, a mainly captured image obtained by imaging the observation object using the white light that is the illumination light of the second pattern, is used in order to more accurately calculate the information on the oxygen saturation carried by the second blue light BL. Hence, the oxygen saturation illumination light is the second blue light BL.

In the case of the correction mode, basically, the light source control unit 22 independently and sequentially turns on the BS light source 20a, the BL light source 20b, the G light source 20c, and the R light source 20d, respectively. Additionally, the light source control unit 22 simultaneously turns on the BS light source 20a, the G light source 20c, and the R light source 20d at least once while, before, or after these respective light sources 20a to 20d are independently turned on, respectively. Hence, in the correction mode, the light source unit 20 sequentially emits the first blue light BS, the second blue light BL, the green light G, and the red light R, and emits the white light at least once during, before, or after emission of each of these color lights. The first blue light BS, second blue light BL, the green light G, and the red light R among such illumination lights are correction illumination lights to be used for the correction of the oxygen saturation observation mode (biological information observation mode). The white light, which is emitted while, before, or after the correction illumination light is emitted, is illumination light for obtaining a white light image 202 (refer to FIG. 15) to be displayed on the monitor 18 in a case where correction images are obtained using the correction illumination light.

In the correction mode of the present embodiment, the correction illumination lights are sequentially turned on in order of the first blue light BS, the second blue light BL, the green light G, and the red light R. Additionally, by certainly emitting the white light one time while each of these correction illumination lights in colors is turned on, the light source unit 20 inserts emission of the white light two or more times. Hence, in the correction mode of the present embodiment as illustrated in FIG. 4, the light source unit 20 emits the first blue light BS, the white light, the second blue light BL, the white light, the green light G, the white light, and the red light R in this order in accordance with the imaging frames. In a case where the correction mode is repeated, this light emission pattern is repeated.

The illumination light emitted from the light source unit 20 is incident on a light guide 41. The light guide 41 is built in the endoscope 12 and a universal cord (a cord that connects the endoscope 12, and the light source device 14 and the processor device 16 to each other), and propagates the illumination light to the distal end part 12d of the endoscope 12. In addition, multimode fiber can be used as the light guide 41. As an example, a fine-diameter fiber cable of which the core diameter is 105 μm, the clad diameter is 125 μm, and a diameter including a protective layer used as an outer cover is ϕ0.3 mm to 0.5 mm can be used.

The distal end part 12d of the endoscope 12 is provided with an illumination optical system 30a and an imaging optical system 30b. The illumination optical system 30a has an illumination lens 45, and the illumination light is radiated to the observation object via the illumination lens 45. The imaging optical system 30b has an objective lens 46, a zoom lens 47, and an image sensor 48. The image sensor 48 images the observation object using reflected light or the like (including scattered light, fluorescence emitted from the observation object, fluorescence due to medicine administered to the observation object, or the like) of the illumination light returning from the observation object via the objective lens 46 and the zoom lens 47. In addition, the zoom lens 47 is moved by operating the zooming operation part 13b, and magnifies or reduces the observation object to be imaged using the image sensor 48.

Figure 5:
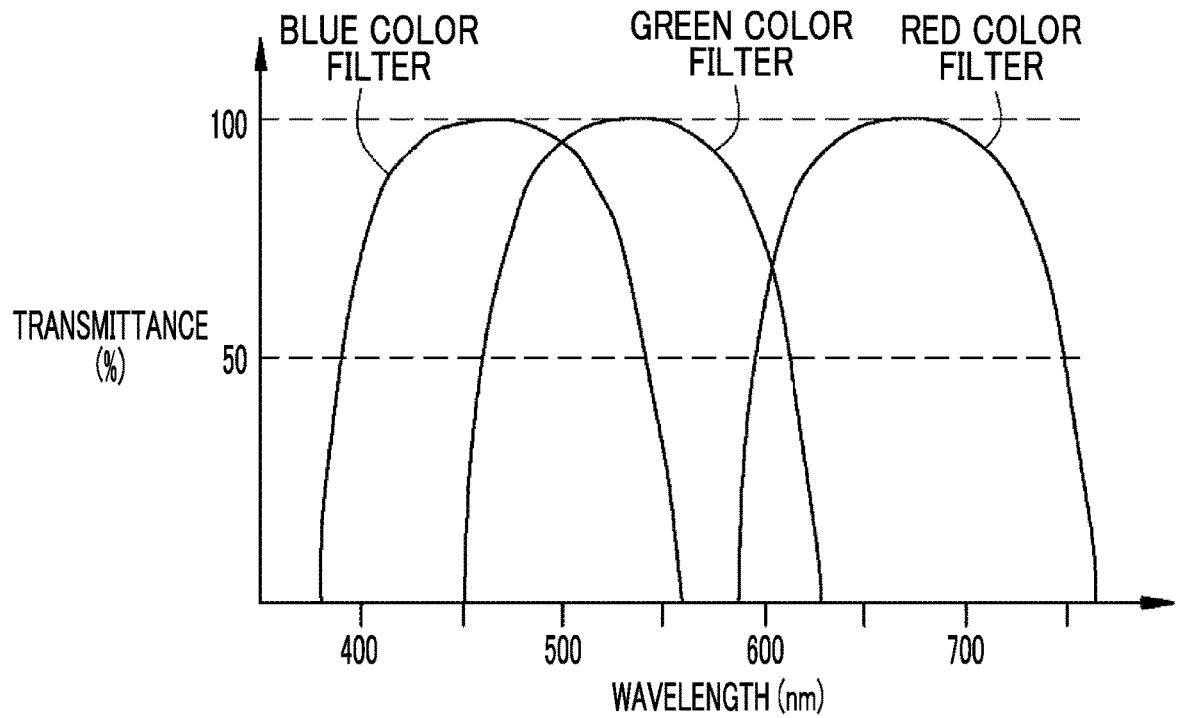
FIG. 5 is a graph illustrating the spectral transmittance of a color filter.

The image sensor 48 is a color sensor of a primary color system, and includes three types of pixels of a blue pixel (B pixel) having a blue (B) color filter, a green pixel (G pixel) having a green (G) color filter, and a red pixel (R pixel) having a red (R) color filter. As illustrated in FIG. 5, a blue color filter allows mainly blue range light, specifically, light in a wavelength range of 380 to 560 nm to be transmitted therethrough. The transmittance of the blue color filter becomes a peak in the vicinity of a wavelength of 460 to 470 nm. The green color filter allows mainly green range light, specifically, light in a wavelength range of 460 to 470 nm to be transmitted therethrough. A red color filter allows mainly red range light, specifically, light in a wavelength range of 580 to 760 nm to be transmitted therethrough.

In a case where the observation object is imaged using the image sensor 48, three types of images of a B image (blue image) shot and obtained in a B pixel, a G image (green image) obtained by being imaged in a G pixel, and an R image (red image) obtained being imaged in an R pixel can be obtained to the maximum in one-time imaging. In the case of the normal observation mode, since the normal observation illumination light to be used is the white light, the Bc image, a Gc image, and an Rc image are obtained as shown in Table 1. The Bc image is an image obtained by imaging the observation object, mainly using reflected light of the first blue light BS, and the like, included in the normal observation illumination light, and the Gc image is an image obtained by imaging the observation object, mainly using reflected light of the green light G, and the like, included in the normal observation illumination light. Similarly, the Rc image is an image obtained by imaging the observation object, mainly using reflected light of the red light R, and the like, included in the normal observation illumination light.

TABLE 1

| Illumination light | Normal observation mode White light | | |
|---|---|---|---|
| Pixel to be imaged | B pixel | G pixel | R pixel |
| Component of corresponding illumination light | First blue light BS | Green light G | Red light R |
| Obtained image | Bc image | Gc image | Rc image |

Meanwhile, in the special observation mode of the present embodiment, in the oxygen saturation observation mode that is the biological information observation mode, and the correction mode, the types and light emission patterns of the illumination light are different from each other. Thus, images are different from each other in the respective modes. In the case of the oxygen saturation observation mode, the illumination light is alternately switched to the second blue light BL (oxygen saturation illumination light) and the white light in accordance with the imaging frames. For this reason, as shown in Table 2, a B1 image, a G1 image, and an R1 image are acquired using the second blue light BL, and a B2 image, a G2 image, and an R2 image are obtained using the white light. The B1 image is an image obtained by imaging the observation object in the B pixel using reflected light of the second blue light BL, and the like. Similarly, the G1 image is an image obtained by imaging the observation object in the G pixel using the reflected light of the second blue light BL, and the like, and the R1 image is an image obtained by imaging the observation object in the R pixel using the reflected light of the second blue light BL, and the like. However, the reflected light of the second blue light BL is hardly transmitted through the green color filter of the G pixel and the red color filter of the R pixel. Thus, in a case where fluorescence or the like is not generated from the observation object, in an imaging frame in which the second blue light BL is used for the illumination light, an image that is substantially obtained is only the B1 image. Additionally, although the same images as those of the normal observation mode are obtained in imaging frames in which the white light is used for the illumination light, respective images obtained in the imaging frames in which the white light is used for the illumination light in the oxygen saturation observation mode are referred to as the B2 image, the G2 image, and the R2 image for the purpose of distinction. In addition, the B1 image, the G1 image, the R1 image, the B2 image, the G2 image, and the R2 image acquired in the oxygen saturation observation mode are mainly captured images.

TABLE 2

| | Oxygen saturation observation mode (Biological information observation mode) | | | | | |
|---|---|---|---|---|---|---|
| | Illumination light | | | | | |
| | Second blue light BL | | | White light | | |
| | Pixel to be imaged | | | | | |
| | B pixel | G pixel | R Pixel | B pixel | G pixel | R Pixel |
| Component of Corresponding Illumination light | Second blue light BL | (Second blue light BL) | (Second blue light BL) | First blue light BS | Green light G | Red light R |
| Obtained image | B1 image | (G1 image) | (R1 image) | B2 image | G2 image | R2 image |

In the case of the correction mode, the illumination light is switched in order of the first blue light BS, the second blue light BL, the green light G, and the red light R in accordance with the imaging frames, and the imaging frames in which the white light is used for the illumination light are inserted therebetween. As shown in Table 3, in an imaging frame in which the first blue light BS is used for the illumination light, a Bp image, a Gp image, and an Rp image are obtained. The Bp image is an image obtained by imaging the observation object in the B image using the reflected light of the first blue light BS, and the like. Similarly, the Gp image is an image obtained by imaging the observation object in the G image using the reflected light of the first blue light, and the like, and the Rp image is an image obtained by imaging the observation object in the R image using the reflected light of the first blue light, and the like. However, the reflected light of the first blue light BS is hardly transmitted through the green color filter of the G pixel and the red color filter of the R pixel. Thus, in a case where fluorescence or the like is not generated from the observation object, in an imaging frame in which the first blue light BS is used for the illumination light, an image that is substantially obtained is only the Bp image.

Additionally, in an imaging frame in which the second blue light BL is used for the illumination light, a Bq image, a Gq image, and an Rq image are obtained. The Bq image is an image obtained by imaging the observation object in the B image using the reflected light of the second blue light BL, and the like. Similarly, the Gq image is an image obtained by imaging the observation object in the G image using the reflected light of the second blue light BL, and the like, and the Rq image is an image obtained by imaging the observation object in the R image using the reflected light of the second blue light BL, and the like. However, the reflected light of the second blue light BL is hardly transmitted through the green color filter of the G pixel and the red color filter of the R pixel. Thus, in a case where fluorescence or the like is not generated from the observation object, in an imaging frame in which the second blue light BL is used for the illumination light, an image that is substantially obtained is only the Bq image.

TABLE 3

| | Correction mode Illumination light | | | | | | |
|---|---|---|---|---|---|---|---|
| | First blue light BS | | | | Second blue light BL | | |
| | Pixel to be imaged | | | | | | |
| | B pixel | G pixel | R pixel | ... | B pixel | G pixel | R pixel | ... |
| Component of corresponding illumination light | First blue light BS | (First blue light BS) | (First blue light BS) | ... | Second blue light BL | (Second blue light BL) | (Second blue light BL) | ... |
| Obtained image | Bp image | (Gp image) | (Rp image) | ... | Bq image | (Gq image) | (Rq image) | ... |

As shown in Table 4, in the correction mode, a Br image, a Gr image, and an Rr image are obtained in an imaging frame in which the green light G is used for the illumination light. The Gr image is an image obtained by imaging the observation object in the G pixel using the reflected light of the green light G, and the like. Similarly, the Br image is an image obtained by imaging the observation object in the B pixel using the reflected light of the green light G, and the like, and the Rr image is an image obtained by imaging the observation object in the R pixel using the reflected light of the green light G, and the like. However, the green light G is hardly transmitted through the blue color filter of the B pixel and the red color filter of the R pixel. Thus, in a case where fluorescence or the like is not generated from the observation object, an image that is substantially obtained is only the Gr image in the imaging frame in which the green light G is used for the illumination light.

Additionally, in the correction mode, a Bs image, a Gs image, and an Rs image are obtained in an imaging frame in which the red light R is used for the illumination light. The Rs image is an image obtained by imaging the observation object in the R pixel using the reflected light of the red light R, and the like. Similarly, the Bs image is an image obtained by imaging the observation object in the B pixel using the reflected light of the red light R, and the like, and the Gs image is an image obtained by imaging the observation object in the G pixel using the reflected light of the red light R, and the like. However, the red light R is hardly transmitted through the blue color filter of the B pixel, and the green color filter of the G pixel. Thus, in a case where fluorescence or the like is not generated from the observation object, an image that is substantially obtained is only the Rs image in the imaging frame in which the red light R is used for the illumination light.

TABLE 4

| | | Correction mode Illumination light | | | | |
|---|---|---|---|---|---|---|
| | | Green light G | | ... | Red light R | |
| | | | Pixel to be imaged | | | |
| | ... B pixel | G pixel | R pixel | ... B pixel | G pixel | R pixel |
| Component of corresponding illumination light | ... (Green light G) | Green light G | (Green light G) | ... (Red light R) | (Red light R) | Red light R |
| Obtained image | ... (Br image) | Gr image | (Rr image) ... | (Bs image) | (Gs image) | Rs image |

Additionally, as shown in Table 5, in the imaging frames in which the white light is used for the illumination light in the correction mode, a Bt image, a Gt image, and an Rt image are obtained. The Bt image is an image obtained by imaging the observation object in the B pixel, mainly using the reflected light of the first blue light BS, and the like, included in the white light. Similarly, the Gt image is an image obtained by imaging the observation object in the G pixel, mainly using the reflected light of the green light G, and the like, included in the white light, and the Rt image is an image obtained by imaging the observation object in the R pixel, mainly using the reflected light of the red light R, and the like, included in the white light. Hence, although these images are the same as the Bc image, the Gc image, and the Rc image obtained in the normal observation mode, these images are referred to as the Bt image, the Gt image, and the Rt image, respectively, for the purpose of distinction. In addition, the Bp image, the Gp image, the Rp image, the Bq image, the Gq image, the Rq image, the Bs image, the Gs image, the Rs image, the Bt image, the Gt image, and the Rt image acquired in the correction mode are the preliminarily captured images. Additionally, the Bp image, the Bq image, the Gr image, and the Rs image among these images are correction images to be actually used for the correction of the oxygen saturation observation mode.

TABLE 5

| | Correction mode | | | |
|---|---|---|---|---|
| Illumination light | ... | White light | | ... |
| Pixel to be imaged | ... B pixel | G pixel | R pixel | ... |
| Component of corresponding illumination light | ... First blue light BS | Green light G | Red light R | ... |
| Obtained image | ... Bt image | Gt imge | Rt image | ... |

In addition, as the image sensor 48, a charge coupled device (CCD) image sensor or a complementary metal-oxide semiconductor (CMOS) image sensor is available. Additionally, although the image sensor 48 of the present embodiment is a color sensor of a primary color system, a color sensor of a complementary color system can also be used. The color sensor of the complementary color system has, for example, a cyan pixel provided with a cyan color filter, a magenta pixel provided with a magenta color filter, a yellow pixel provided with a yellow color filter, and a green pixel provided with a green color filter. Images obtained from the above respective pixels in colors in a case where the color sensor of the complementary color system is used can be converted into the B image, the G image, and the R image in a case where complementary color-primary color conversion is performed. Additionally, instead of the color sensor, a monochrome sensor that is not provided with the color filters may be used as the image sensor 48. In this case, the above respective color images can be obtained by sequentially imaging the observation object using the respective illumination lights in colors, such as BGR.

The processor device 16 has a control unit 52, an image acquisition unit 54, an image processing unit 61, and a display control unit 66.

The control unit 52 switches between the observation modes by receiving input of a mode switching signal from the mode changeover switch 13a, and inputting control signals to the light source control unit 22 and the image sensor 48. Additionally, in the special observation mode, switching is made between the oxygen saturation observation mode and the correction mode. In addition, the control unit 52 also synchronously controls the radiation timing of the illumination light, the timing of the imaging, and the like.

The image acquisition unit 54 acquires an image of the observation object from the image sensor 48. In the case of the normal observation mode, the image acquisition unit 54 acquires the Bc image, the Gc image, and the Rc image for each imaging frame. In the case of the special observation mode of the present embodiment, in the oxygen saturation observation mode (biological information observation mode), the image acquisition unit 54 acquires the B1 image, the G1 image, and the R1 image in the imaging frame in which the second blue light BL is used for the illumination light, and acquires the B2 image, the G2 image, and the R2 image in the imaging frames in which the white light is used for the illumination light. Meanwhile, in the correction mode, the image acquisition unit 54 acquires the Bp image, the Gp image, and the Rp image in the imaging frame in which the first blue light BS is used for the illumination light, acquires the Bq image, the Gq image and the Rq image in the imaging frame in which the second blue light BL is used for the illumination light, acquires the Br image, the Gr image, and the Rr image in the imaging frame in which the green light G is used for the illumination light, and acquires the Bs image, the Gs image, and the Rs image in the imaging frame in which the red light R is used for the illumination light. Moreover, in the imaging frames which are inserted between the above frames and in which the white light is used for the illumination light, the Bt image, the Gt image, and the Rt image are acquired.

Additionally, the image acquisition unit 54 has a digital signal processor (DSP) 56, a noise reduction unit 58, and a converting unit 59, and performs various kinds of processing on an acquired image using these units.

The DSP 56 performs various kinds of processing, such as defect correction processing, offset processing, gain correction processing, linear matrix processing, gamma conversion processing, demosaicing processing, and YC conversion processing, on the acquired image, as needed.

The defect correction processing is the processing of compensating for the pixel value of a pixel corresponding to a defective pixel of the image sensor 48. The offset processing is the processing of reducing a dark current component from the image subjected to the defect correction processing, and setting an accurate zero level. The gain correction processing is the processing of adjusting a signal level of each image by multiplying the image subjected to the offset processing by a gain. The linear matrix processing is the processing of enhancing color reproducibility on the image subjected to the offset processing, and the gamma conversion processing is the processing of adjusting the brightness or saturation of the image after the linear matrix processing. The demosaicing processing (also referred to as equalization processing or synchronization processing) is the processing of interpolating the pixel value of a missing pixel, and is performed on the image after the gamma conversion processing. The missing pixel is a pixel with no pixel value because pixels in other colors are disposed in the image sensor 48 due to the arrangement of color filters. For example, since the B image is an image obtained by imaging the observation object in the B pixel, there is no pixel value in pixels at positions corresponding to the G pixel and the R pixel of the image sensor 48. In the demosaicing processing, the pixel values of the pixels at the positions of the G pixel and the R pixel of the image sensor 48 are generated by interpolating the B image. The YC conversion processing is the processing of converting the image after the demosaic processing into a luminance channel Y, a color difference channel Cb, and a color difference channel Cr.

The noise reduction unit 58 performs noise reduction processing using, for example, a moving average method, a median filter method, or the like, on the luminance channel Y, the color difference channel Cb, and the color difference channel Cr. The converting unit 59 re-converts the luminance channel Y, the color difference channel Cb, and the color difference channel Cr after the noise reduction processing into images in respective colors of BGR.

The image processing unit 61 has a normal processing unit 62 and a special processing unit 63. The normal processing unit 62 operates in the normal observation mode, and performs color conversion processing, color enhancement processing, and structure enhancement processing on the Bc image, the Gc image, and the Rc image, equivalent to one imaging frame, subjected to the above various kinds of processing to generate a normal image. In the color conversion processing, 3×3 matrix processing, gradation transformation processing, three-dimensional look-up table (LUT) processing, and the like are performed on the images in the respective colors of BGR. The color enhancement processing is the processing of enhancing the colors of an image, and the structure enhancement processing is the processing of enhancing, for example, the tissue or structure of the observation object, such as blood vessels or pit patterns. The display control unit 66 sequentially acquires normal images from the normal processing unit 62, converts the acquired normal images into a format suitable for display, and sequentially outputs and displays the converted images to and on the monitor 18. Accordingly, in the case of the normal observation mode, a doctor or the like can observe the observation object using a motion picture of the normal images.

Figure 6:
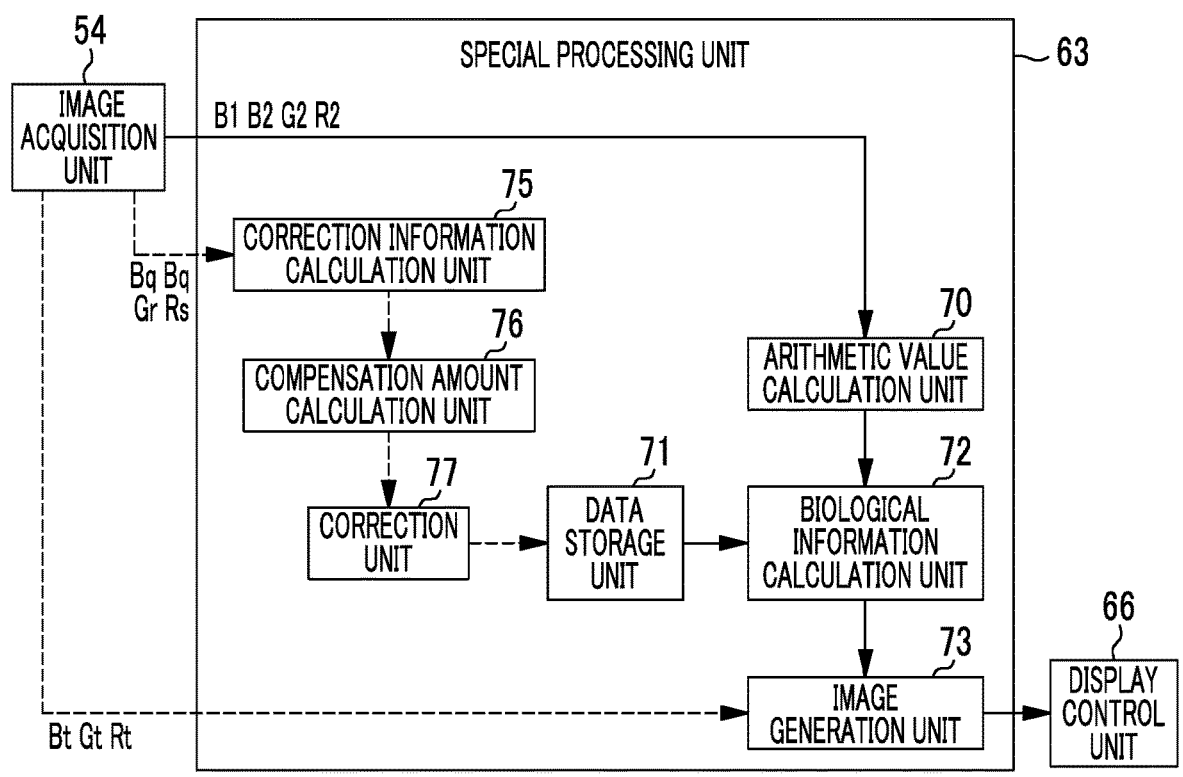
FIG. 6 is a block diagram of a special processing unit.

As illustrated in FIG. 6, the special processing unit 63 includes an arithmetic value calculation unit 70, a data storage unit 71, a biological information calculation unit 72, an image generation unit 73, a correction information calculation unit 75, a compensation amount calculation unit 76, and a correction unit 77. The arithmetic value calculation unit 70, the biological information calculation unit 72, and the image generation unit 73 among these units function in the oxygen saturation observation mode.

The arithmetic value calculation unit 70 acquires mainly captured images obtained in the biological information observation mode from the image acquisition unit 54, and calculates arithmetic values that the biological information calculation unit 72 uses for the calculation of the biological information using the mainly captured images. That is, since the biological information observation mode is the oxygen saturation observation mode in which the oxygen saturation is calculated as the biological information, the arithmetic value calculation unit 70 acquires the mainly captured images obtained in the oxygen saturation observation mode from the image acquisition unit 54, and calculates arithmetic values that the biological information calculation unit 72 uses for the calculation of the oxygen saturation using the mainly captured images. More specifically, the arithmetic value calculation unit 70 acquires the B1 image, the B2 image, the G2 image, and the R2 image from the image acquisition unit 54 in the oxygen saturation observation mode. Then, a ratio B1/G2 of the B1 image to the G2 image and a ratio R2/G2 of the R2 image to the G2 image are calculated for each pixel, respectively. The ratio B1/G2 and the ratio R2/G2 are arithmetic values used for the calculation of the oxygen saturation.

Figure 7:
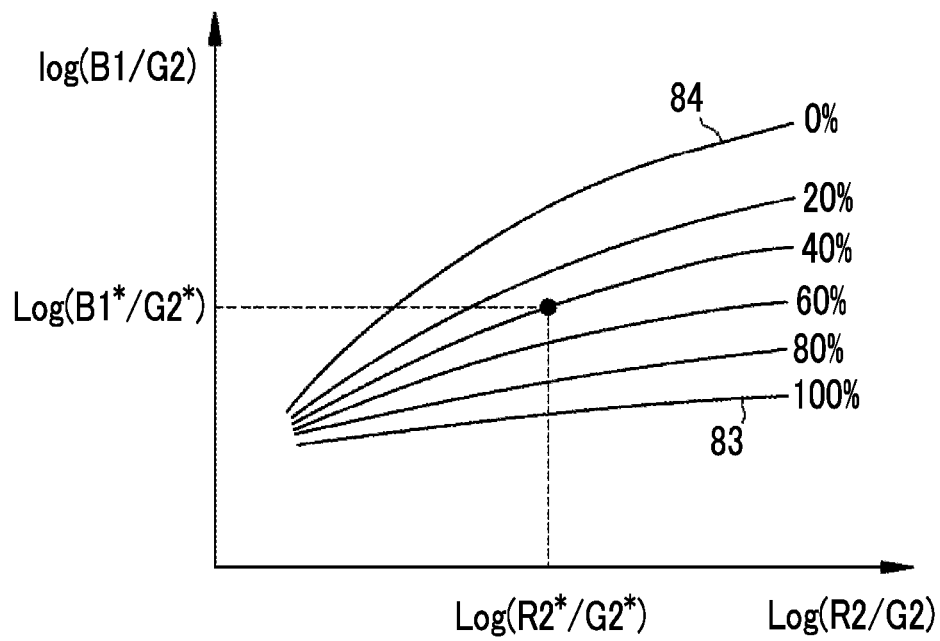
FIG. 7 is a first feature space representing a correlation between arithmetic values and oxygen saturation.

The data storage unit 71 stores data to be used in a case where the biological information calculation unit 72 calculates the biological information using the above arithmetic values calculated by the arithmetic value calculation unit 70. That is, since the oxygen saturation is calculated as the biological information, the data storage unit 71 stores a correlation between the above arithmetic values calculated by the arithmetic value calculation unit 70 and the oxygen saturation in the form of an LUT or the like. As illustrated in FIG. 7, in a case where this correlation is expressed in a first feature space formed using a vertical axis Log (B1/G2)

and a horizontal axis Log (R2/G2), isoplethic lines obtained by connecting points with oxygen saturation values together are formed substantially in a lateral direction. Additionally, the isoplethic lines are located closer to a lower side in a vertical axis direction as the oxygen saturation becomes larger. For example, an isoplethic line 83 having an oxygen saturation of 100% is located below an isoplethic line 84 having an oxygen saturation of 0%.

Figure 8:
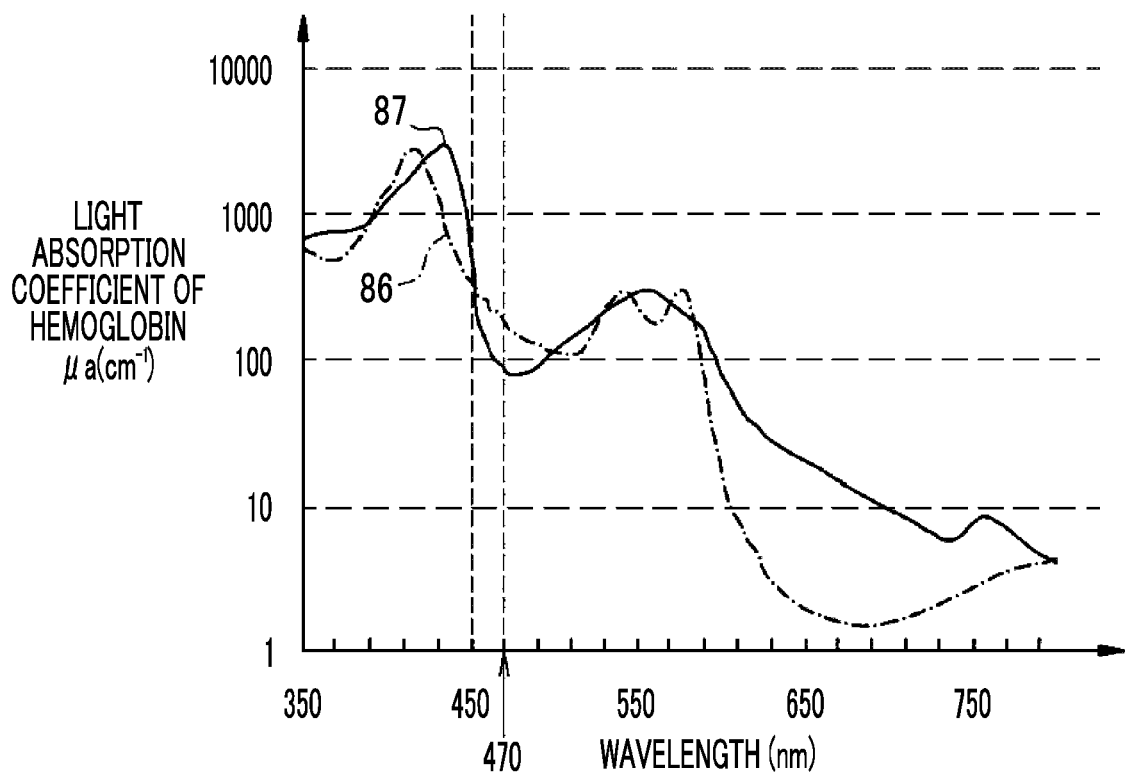
FIG. 8 is a graph illustrating the light absorption coefficients of oxygenated hemoglobin and reduced hemoglobin.

The above correlation is closely correlated with light-absorption characteristics of oxygenated hemoglobin (graph 86) and reduced hemoglobin (graph 87) that are illustrated in FIG. 8. Specifically, in the wavelength (about 470±10 nm) of the second blue light BL, the difference between the light absorption coefficients of the oxygenated hemoglobin and the reduced hemoglobin is large. Thus, light absorption amount varies due to the oxygen saturation of hemoglobin. For this reason, in the second blue light BL, it is easy to handle information on the oxygen saturation. Hence, the oxygen saturation can be calculated in a case where the ratio B1/G2 obtained by standardizing the B1 image using the G2 image for compensation of illuminance unevenness or the like, is used. However, the ratio B1/G2 depends on not only the oxygen saturation but also the amount of blood. Thus, by using the ratio R2/G2 that varies mainly depending on the amount of blood in addition to the ratio B1/G2, the oxygen saturation can be calculated without being influenced by the amount of blood. In addition, the wavelength (about 540±20 nm) of the green light G included in the G2 image is a wavelength where the light absorption coefficient is apt to vary due to the amount of blood because the light absorption coefficient of hemoglobin is relatively high.

In addition, the positions and the shapes of the isoplethic lines in the above first feature space are obtained in advance as a result of performing physical simulation of light scattering. Additionally, although the data storage unit 71 stores the correlations between the ratio B1/G2 and the ratio R2/G2, and the oxygen saturation, the data storage unit 71 may store other correlations. For example, in a case where the oxygen saturation is calculated using arithmetic values (hereinafter referred to as other arithmetic values) obtained as a result of performing other calculation (for example, difference processing) different from the above description based on the B1 image, the B2 image, the G2 image, and the R2 image, the data storage unit 71 may store the correlation in which the other arithmetic values are matched with the oxygen saturation.

The biological information calculation unit 72 refers to the data stored in the data storage unit 71, and calculates and the like the biological information using the arithmetic values calculated by the arithmetic value calculation unit 70. In the present embodiment, the biological information calculation unit 72 functions as an oxygen saturation calculation unit. Specifically, the biological information calculation unit 72 refers to the correlation stored in the data storage unit 71, and calculates an oxygen saturation corresponding to the ratio B1/G2 and the ratio R2/G2 for each pixel. For example, an oxygen saturation corresponding to a ratio B1*/G2* and a ratio R2*/G2* of a specific pixel is "40%" in a case where the correlation stored in the data storage unit 71 is referred to. Hence, the biological information calculation unit 72 calculates the oxygen saturation of this specific pixel to be "40%".

In addition, the ratio B1/G2 and R2/G2 hardly become extremely large or extremely small. That is, the combination of the respective values of the ratios B1/G2 and the ratio R2/G2 is hardly distributed below the isoplethic line 83 (refer to FIG. 7) of an upper limit that is an oxygen saturation of 100% or conversely, the combination is hardly distributed above the isoplethic line 84 (refer to FIG. 7) of a lower limit that is an oxygen saturation of 0%. In a case where the combination of the respective values of the ratio B1/G2 and the ratio R2/G2 is distributed below from the maximum isoplethic line 83, the biological information calculation unit 72 calculates the oxygen saturation of the pixel to be 100%. Similarly, in a case where the combination of the respective values of the ratio B1/G2 and the ratio R2/G2 is distributed above the isoplethic line 84 of the lower limit, the biological information calculation unit 72 calculates the oxygen saturation of the pixel to be 0%. Additionally, in a case where a point corresponding to the ratio B1/G2 and the ratio R2/G2 is not distributed between the isoplethic line 83 of the upper limit and the isoplethic line 84 of the lower limit, a display may be performed such that the reliability of the oxygen saturation in the pixel is low, and the oxygen saturation may not be calculated.

In the case of the biological information observation mode, the image generation unit 73 generates a biological information image showing the biological information calculated by the biological information calculation unit 72. That is, the image generation unit 73 generates the oxygen saturation image obtained by turning the oxygen saturation into an image using the oxygen saturation calculated in the biological information calculation unit 72. Specifically, the image generation unit 73 acquires the B2 image, the G2 image, and the R2 image, and gives a gain according to the oxygen saturation to these images for each pixel. For example, the image generation unit 73 multiplies all the B2 image, the G2 image, and the R2 image by the same gain "1" in pixels with an oxygen saturation of 60% or more. In contrast, in pixels with an oxygen saturation of less than 60%, the B2 image is multiplied by a gain of less than "1", and the G2 image and the R2 image are multiplied by a gain of "1" or more. Thereafter, the image generation unit 73 generates an oxygen saturation image in color using the B2 image, the G2 image, and the R2 image to which the gain is given as described above. Oxygen saturation images generated by the image generation unit 73 are acquired by the display control unit 66, and are sequentially displayed on the monitor 18.

In each oxygen saturation image generated by the image generation unit 73, a high-oxygen region (in the present embodiment, a region where the oxygen saturation is 60 or more and 100% or less) is expressed in natural colors, similar to the normal image. On the other hand, a low-oxygen region where the oxygen saturation is less than a specific value (in the present embodiment, a region where the oxygen saturation is 0 or more and 60% or less) is expressed in colors (pseudo-colors) different from the normal image. In addition, in the present embodiment, in the case of the oxygen saturation observation mode, the image generation unit 73 multiplies the low-oxygen region only by a gain for pseudo-coloring. However, the gain according to the oxygen saturation may also be given to the high-oxygen region, and the overall oxygen saturation image may be pseudo-colored. Additionally, although the low-oxygen region and the high-oxygen region are divided with an oxygen saturation of 60% as a boundary, any boundary may also be adopted.

Meanwhile, in the correction mode, the correction information calculation unit 75, the compensation amount calculation unit 76, the correction unit 77, and the image generation unit 73 among the respective units of the special processing unit 63 function.

The correction information calculation unit 75 acquires the preliminarily captured images from the image acquisition unit 54, and calculates biological information to be used for correction (hereinafter referred to correction information) in the biological information observation mode using the preliminarily captured images. The correction information is, for example, biological information peculiar to the observation object representing the part, state, and the like of the observation object. Specifically, the correction information calculation unit 75 first acquires at least the Bp image, the Bq image, the Gr image, and the Rs image from the image acquisition unit 54. Then, biological information relating to a yellow coloring agent (bilirubin, stercobilin, or the like) adhering to the observation object and having low dependability on the oxygen saturation, and the other biological information to be used for the correction of the oxygen saturation observation mode are calculated. The expression "relating to a yellow coloring agent" means that there is a correlation with the adhesion amount or concentration of the yellow coloring agent. The expression "having low dependability on the oxygen saturation" means that the value of the yellow coloring agent information does not vary substantially due to the value of the oxygen saturation.

More specifically, the correction information calculation unit 75 first calculates a ratio Bp/Gr of the Bp image to the Gr image, a ratio Bq/Gr of to the Bq image to the Gr image, and a ratio Rs/Gr of the Rs image to the Gr image for each pixel.

Figure 9:
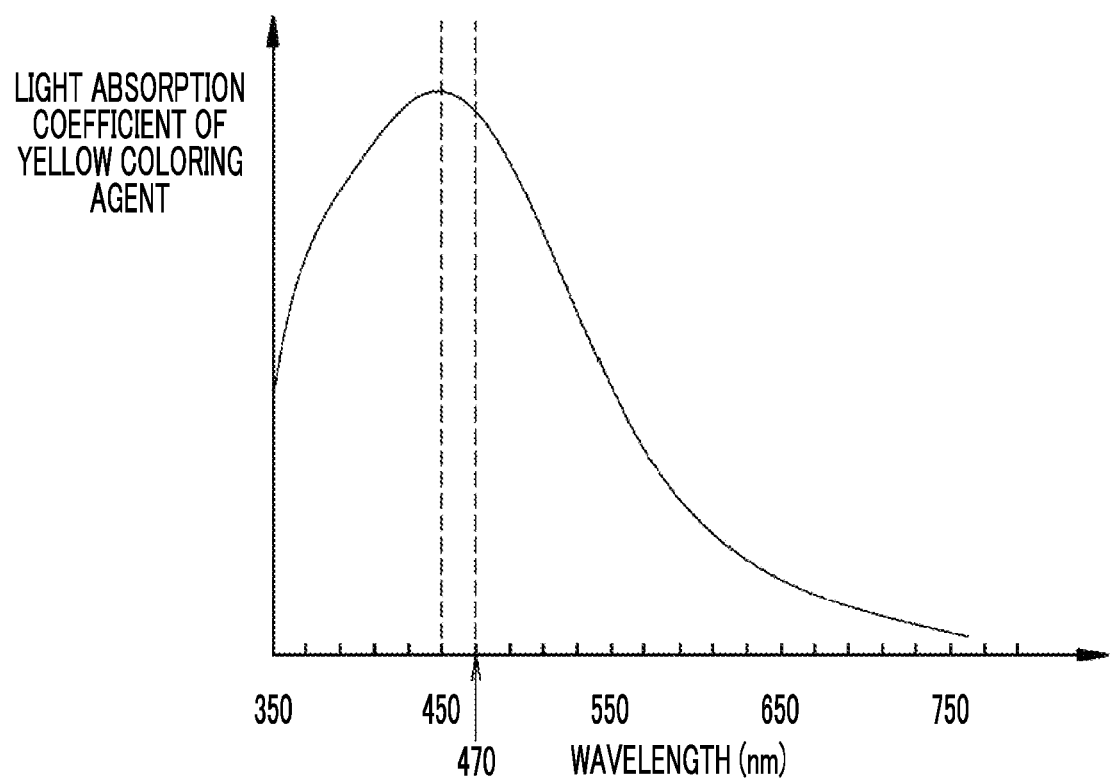
FIG. 9 is a graph illustrating the light absorption coefficient of a yellow coloring agent.

The Bp image is an image corresponding to the first blue light BS, and the wavelength range (a central wavelength of about 450±10 nm) of the first blue light BS is an equal absorption wavelength in which the light absorption coefficient of hemoglobin is relatively high and the light absorption coefficients of the oxygenated hemoglobin and the reduced hemoglobin are approximately equal to each other (refer to FIG. 8). For this reason, the Bp image is an image of which the values are not apt to vary due to the oxygen saturation. Additionally, since the first blue light BS has a wavelength range where the light absorption coefficient of the yellow coloring agent is approximately the highest as illustrated in FIG. 9, the light absorption amount is apt to vary in accordance with the adhesion amount or concentration of the yellow coloring agent. From these facts, the value of the ratio Bp/Gr obtained by standardizing the Bp image using the Gr image for the compensation of the illuminance unevenness or the like, hardly varies due to the oxygen saturation but varies due to the adhesion amount or concentration of the yellow coloring agent. In addition, since the wavelength range of the green light G corresponding to the Gr image is a wavelength range where the light absorption amount is apt to vary due to the amount of blood, the ratio Bp/Gr varies due to the amount of blood.

Additionally, the Bq image is an image corresponding to the second blue light BL, and the wavelength range (about 470±10 nm) of the second blue light BL is the wavelength range in which the light absorption coefficient of hemoglobin is relatively high and the light absorption coefficients of the oxygenated hemoglobin and the reduced hemoglobin are different from each other (refer to FIG. 8). For this reason, the Bq image is an image that is apt to vary due to the oxygen saturation. Additionally, the wavelength range of the second blue light BL is slightly shifted from the absorption peak of the yellow coloring agent, but has a large light absorption coefficient compared to other wavelength ranges (refer to FIG. 9). From these facts, the value of the ratio Bp/Gr obtained by standardizing the Bq image using the Gr image for the compensation of the illuminance unevenness or the like, varies due to the oxygen saturation, and the adhesion amount or concentration of the yellow coloring agent. Additionally, since the Gr image has dependability on the amount of blood, the value of the ratio Bq/Gr varies due to the amount of blood.

Meanwhile, the Rs image is an image corresponding to the red light R, and the wavelength range (a central wavelength of about 640±20 nm) of the red light R is a wavelength range where the light absorption coefficient of hemoglobin is very small compared to the wavelength range of the first blue light BS or the second blue light BL (refer to FIG. 8). For this reason, in the Rs image, there is a difference between the light absorption coefficients of the oxygenated hemoglobin and the reduced hemoglobin. However, since the light absorption amount is excessively small, there is substantially no dependability on the oxygen saturation. Additionally, also regarding the yellow coloring agent, the light absorption coefficient of the yellow coloring agent in the wavelength range of the red light R is an extremely small value compared to the wavelength range of the first blue light BS or the second blue light B. Thus, the Rs image hardly varies due to the adhesion amount or concentration of the yellow coloring agent. Hence, the value of the ratio Rs/Gr obtained by standardizing the Rs image using the Gr image for the compensation of the illuminance unevenness or the like, hardly depends on the oxygen saturation, or the adhesion amount or concentration of the yellow coloring agent. However, the ratio Rs/Gr varies due to the amount of blood, reflecting the dependability of the Gr image on the amount of blood.

From the above fact, at least the ratio Bp/Gr corresponds to biological information relating to the yellow coloring agent adhering to the observation object and having low dependability on the oxygen saturation. However, in the present embodiment, the correction information calculation unit 75 calculates biological information (hereinafter referred to as yellow coloring agent information) Vy which is more accurately relating to the yellow coloring agent adhering to the observation object and lower dependability on the oxygen saturation, on the basis of following Equation A. The phase $\phi$ is a known amount adjusted in advance such that the yellow coloring agent information Vy obtained by the calculation based on Equation A become constant even though the oxygen saturation varies. The correction information calculation unit 75 inputs the yellow coloring agent information Vy after the adjustment of the phase $\phi$, and the ratio Rs/Gr, to the compensation amount calculation unit 76 as the correction information.

$$Vy=(Bp/Gr)\times\cos\phi+(Bq/Gr)\times\sin\phi \qquad \text{[Equation A]}$$

The compensation amount calculation unit 76 calculates the compensation amount of the data to be used for the calculation of the biological information from predetermined reference information, and the correction information calculated by the correction information calculation unit 75. That is, the compensation amount calculation unit 76 calculates the compensation amount $\Delta D$ of the correlation used for the calculation of the oxygen saturation using the yellow coloring agent information Vy. Additionally, by using the correction information calculated by the correction information calculation unit 75, the compensation amount calculation unit 76 substantially uses the correction images for the calculation of the compensation amount. In the case of the present embodiment, the reference information is the correlation between the yellow coloring agent information Vy acquired in a state where there is almost no yellow coloring agent, and the ratio Rs/Gr. The yellow coloring agent information Vy constituting the reference information is the yellow coloring agent information Vy calculated in accordance with Equation A by adjusting the phase φ such that there is no change resulting from the oxygen saturation using the Bp image, the Bq image, and the Gr image acquired in a state where there is substantially no yellow coloring agent. In this process, the phase φ of Equation A is also determined. As the reference information, for example, a phantom obtained by imitating a living body can be determined in advance by imaging, simulation, or the like. In addition, the data to be used for the calculation of the biological information in the biological information observation mode as above is the correlation stored in the data storage unit 71 store in the present embodiment.

Figure 10:
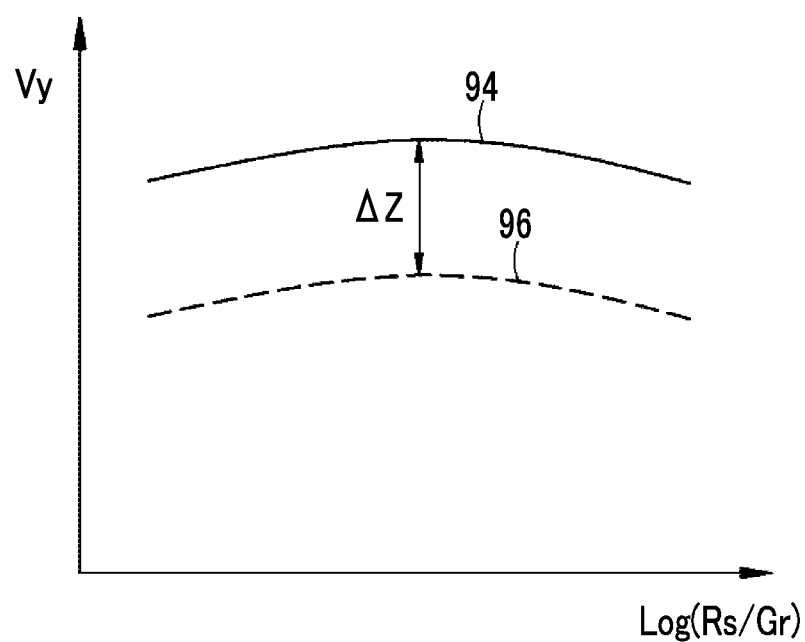
FIG. 10 is a second feature space to be used for calculation of a compensation amount.

As illustrated in FIG. 10, the compensation amount calculation unit 76 calculates the compensation amount ΔD using the second feature space in which the vertical axis is the yellow coloring agent information Vy, and the horizontal axis is Log(Rs/Gr). Since the ratio Rs/Gr to be used for the horizontal axis represents the amount of blood, the second feature space represents the distribution of the yellow coloring agent information Vy with respect to the amount of blood, and a line connecting points where the yellow coloring agent information Vy is equal in the second feature space is an isoplethic line (hereinafter referred to as an equal concentration line) in which the concentrations (or adhesion amounts) of the yellow coloring agent are equal to each other.

The reference information forms a referential equal concentration line 94 in the second feature space. For this reason, in a case where there is actually no yellow coloring agent, points where the yellow coloring agent information Vy and the ratio Rs/Gr obtained by actually and preliminarily capturing the observation object are determined within the second feature space lie on the referential equal concentration line 94. However, in a case where there is a yellow coloring agent, the points lie on an equal concentration line 96 shifted from a referential equal concentration line 94 due to the adhesion amount or concentration of the yellow coloring agent. Hence, in the second feature space, the equal concentration line 96 on which the points represented by the yellow coloring agent information Vy and the ratio Rs/Gr obtained by actually preliminarily capturing the observation object lie, the referential equal concentration line 94, and a difference Δ in the vertical axis direction represent the adhesion amount or concentration of the yellow coloring agent. Hence, the compensation amount calculation unit 76 calculates the compensation amount ΔD (=ΔZ×α) by calculating the difference ΔZ between line the referential equal concentration line 94 and the equal concentration line 96 and multiplying the difference by a predetermined coefficient α. In addition, the coefficient α is a value for scale-converting the difference ΔZ into a value suitable for the compensation of the correlation stored in the data storage unit 71. Since the value of the yellow coloring agent information Vy becomes larger as the adhesion amount or concentration of the yellow coloring agent is smaller, the equal concentration line of the second feature space is formed below the referential equal concentration line 94.

The correction unit 77 corrects the biological information observation mode by compensating for the data to be used for the calculation and the like of the biological information using the compensation amount ΔD calculated by the compensation amount calculation unit 76. In the present embodiment, the correction unit 77 corrects the oxygen saturation observation mode by compensating for the correlation stored in the data storage unit 71 using the compensation amount ΔD. Specifically, the correction unit 77 adds the compensation amount ΔD to the value of Log (B1/G2) of the vertical axis on all the isoplethic lines in the first feature space (refer to FIG. 7). That is, the correction unit 77 shifts all the isoplethic lines of the first feature space upward on the vertical axis by the compensation amount ΔD. In this way, an error factor (in the present embodiment, the adhesion amount or concentration of the yellow coloring agent), such as a part or an actual state, which is peculiar to an actual observation object, is reflected in the first feature space compensated for by the correction unit 77. Hence, in the oxygen saturation observation mode, the biological information calculation unit 72 can calculate an accurate oxygen saturation that does not depend on the error factor peculiar to the observation object by using the first feature space compensated for by the correction unit 77.

As described above, while the biological information observation mode (oxygen saturation observation mode) is corrected using the correction information calculation unit 75, the compensation amount calculation unit 76, and the correction unit 77, the image generation unit 73 sequentially acquires the Bt image, the Gt image, and the Rt image (that is, images obtained using the white light during the correction mode) from the image acquisition unit 54 in the correction mode. Then, the image generation unit 73 performs the color conversion processing, the color enhancement processing, and the structure enhancement processing on the Bt image, the Gt image, and the Rt image equivalent to one imaging frame, and generates the white light image 202. The white light image 202 is the same as the normal image of the normal observation mode except that the white light image is generated during the correction mode. Hence, in a case where the white light image 202 is used, the natural-tone observation object can be observed.

In the correction mode, the display control unit 66 sequentially acquires the above white light images 202 generated by the image generation unit 73, and displays the acquired images on the monitor 18. For this reason, the observation of the observation object can be continued without interruption using the white light image 202 or a motion picture including the white light images 202, in the midst of capturing the preliminarily captured images in the correction mode.

Figure 11:
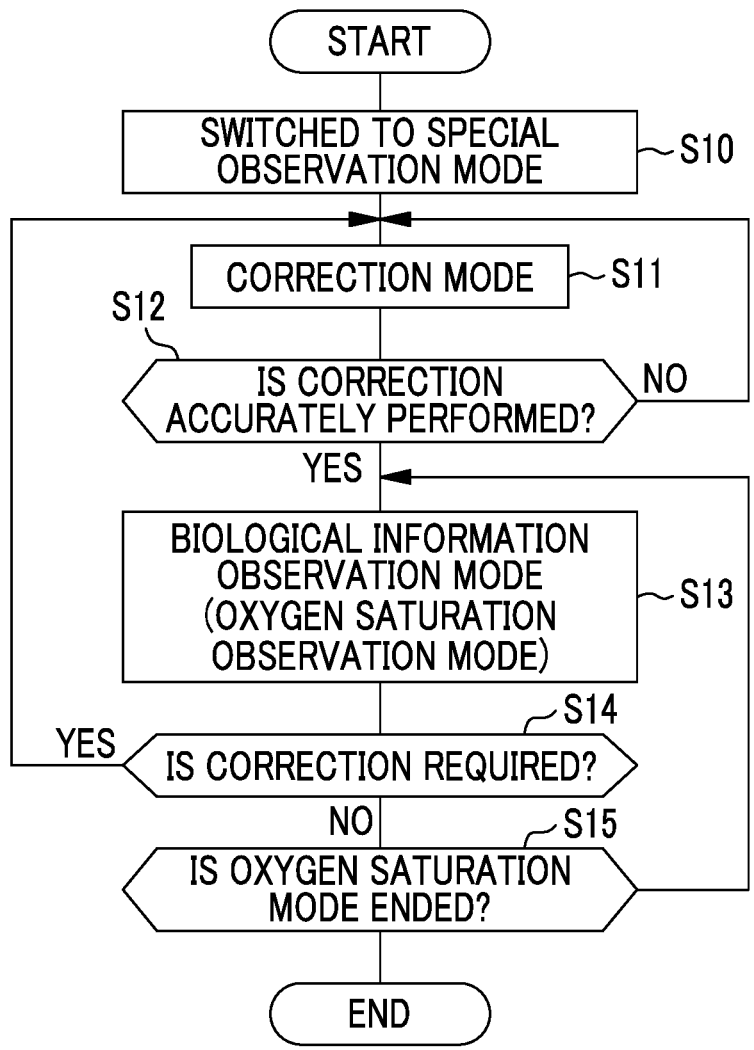
FIG. 11 is a flowchart illustrating a flow of operation of the special observation mode.

Next, a flow of a series of operation of the special observation mode will be described along a flowchart illustrated in FIGS. 11 to 13. First, in a case where the mode changeover switch 13a is operated to switch to the special observation mode as illustrated in FIG. 11 (S10), the control unit 52 executes the correction mode by inputting control signals to the light source control unit 22 and the image sensor 48 (S11). In the correction mode, the oxygen saturation observation mode (biological information observation mode) is corrected by compensating for the correlation to be used for the calculation of the oxygen saturation using the preliminarily captured images obtained by the preliminary capturing. Moreover, in the correction mode, while the preliminarily captured images are obtained, the observation object is imaged using the white light, and the white light image 202 is displayed on the monitor 18. For this reason, the doctor or the like views the white light image 202 (or a motion picture including the white light images 202), and determines whether or not the correction the oxygen saturation observation mode has been accurately performed (S12). Specifically, since the correction of the oxygen saturation is accurately performed in a case where the preliminary capturing is performed under unsuitable conditions, it is checked that the preliminary capturing has been appropriately performed while viewing the white light image 202 displayed on the monitor 18 during the correction mode. For example, conditions regarding an imaging position, such as whether or not there is any clear lesion in the observation object, and conditions regarding imaging situations, such as whether or the not the brightness is suitable, or whether the observation object is not clear due to movement of the observation object are determined from the white light image 202 obtained substantially simultaneously with the preliminarily captured images.

In a case where it is determined from the white light image 202 that there is a possibility that the preliminary capturing is not appropriately performed and the biological information observation mode is not accurately corrected (S12: NO), the correction mode is again executed by an operation input from the console 19 or the like. On the other hand, in a case where it is determined from the white light image 202 that the preliminary capturing is appropriately performed and the biological information observation mode can be accurately corrected in accordance with the observation object (S12: YES), the process proceeds to the oxygen saturation observation mode that is the biological information observation mode of the present embodiment by an operation input from console 19 or the like (S13). In the oxygen saturation observation mode, the endoscope system 10 calculates the oxygen saturation using the mainly captured images obtained by performing the main capturing, and displays the oxygen saturation image showing the values of the oxygen saturation using pseudo-colors, on the monitor 18. For this reason, the doctor or the like views and diagnoses the oxygen saturation image. In a case where diagnosing using the oxygen saturation image, in a case where there is a doubt about shown values of the oxygen saturation, such as the values of the oxygen saturation are high as a whole or low as a whole and it is necessary to perform the correction again (S14), the process proceeds to the correction mode (S13) by an operation input from the console 19 or the like, and the oxygen saturation observation mode is corrected again. Additionally, the endoscope system 10 repeatedly executes the oxygen saturation observation mode by the operation of the mode changeover switch 13a until the oxygen saturation observation mode is ended (S15), and continuously displays oxygen saturation images on the monitor 18.

Figure 12:
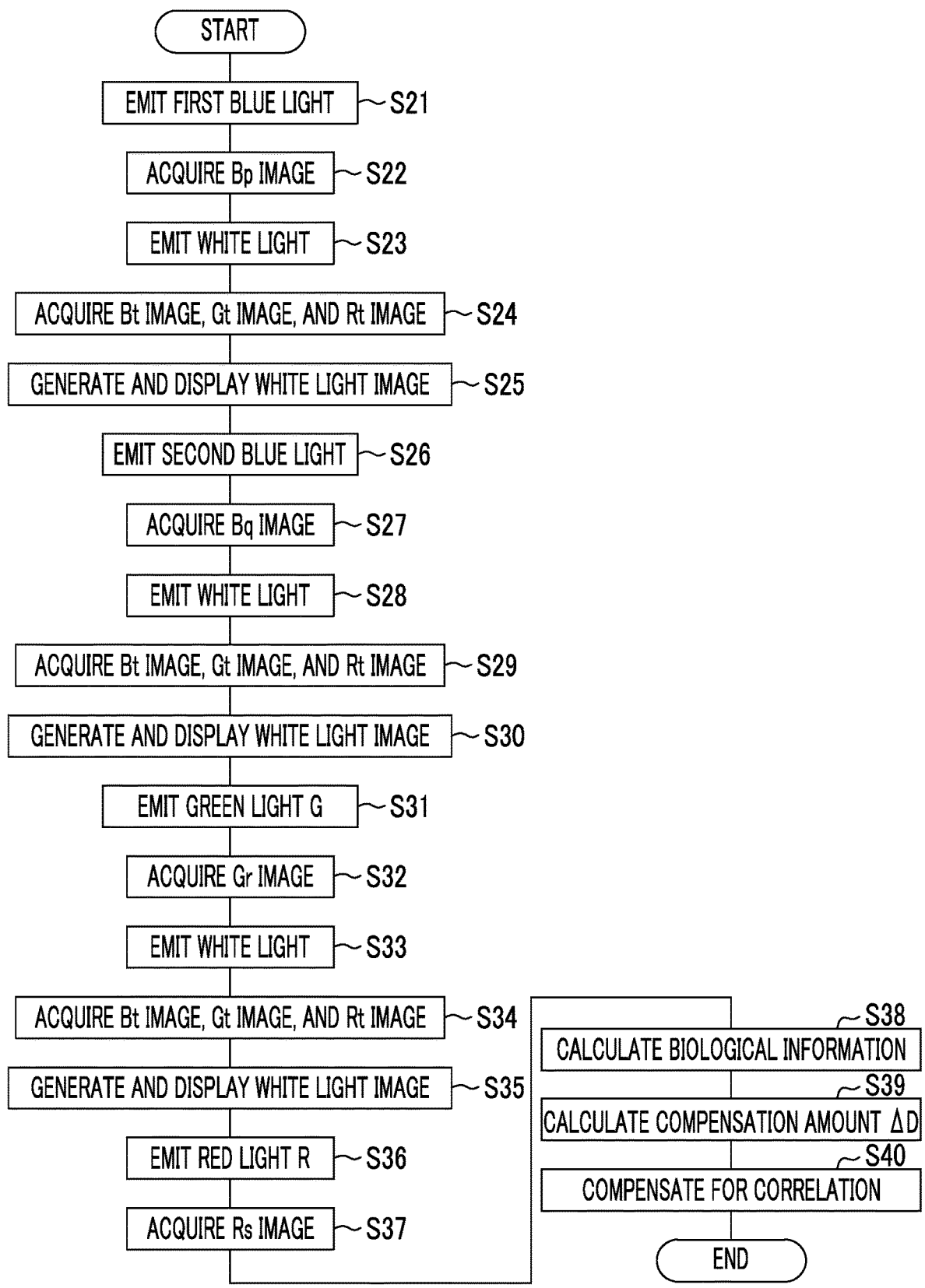
FIG. 12 is a flowchart illustrating a flow of the operation of a correction mode.

As illustrated in FIG. 12, in the correction mode (Step S11 of FIG. 11), first, the light source unit 20 emits the first blue light BS (S21), image sensor 48 automatically preliminarily captures the observation object using the first blue light BS, and the image acquisition unit 54 acquires the Bp image to be used for the correction of the oxygen saturation observation mode (S22). Next, the light source unit 20 emits the white light (S23). For this reason, in the next imaging frame in which the Bp image is obtained, the image sensor 48 automatically images the observation object using the white light, and the image acquisition unit 54 acquires the Bt image, the Gt image, and the Rt image (S24). Although in the middle of the preliminary capturing, the image generation unit 73 generates a white light image 202 using the Bt image, the Gt image, and the Rt image obtained here, and the display control unit 66 displays the white light image 202 on the monitor 18 (S25).

In an imaging frame next to the imaging frame in which the white light image 202 is obtained, the light source unit 20 emits the second blue light BL (S26). Then, the image sensor 48 automatically images the observation object using second blue light BL, and the image acquisition unit 54 acquires the Bq image required for the correction of the oxygen saturation observation mode (S27). In the next imaging frame in which the Bq image is obtained, the light source unit 20 does not emit the illumination light for obtaining the next preliminarily captured images but emits the white light again (S28). For this reason, the image sensor 48 images the observation object using the white light, and the image acquisition unit 54 acquires the Bt image, the Gt image, and the Rt image again (S29). The image generation unit 73 generates a white light image 202 from the Bt image, the Gt image, and the Rt image, and the display control unit 66 displays the generated white light image 202 on the monitor 18 (S30).

In the next imaging frame, the light source unit 20 emits the green light G (S31). Then, the image sensor 48 automatically images the observation object using the green light G, and the image acquisition unit 54 acquires the Gr image required for the correction of the oxygen saturation observation mode (S32). Next, the light source unit 20 emits the white light again (S33), an image sensor 48 automatically images the observation object using the white light, and the image acquisition unit 54 acquires the Bt image, the Gt image, and the Rt image (S34). For this reason, the image generation unit 73 generates a white light image 202 using these images, and the display control unit 66 displays the white light image 202 on the monitor 18 (S35).

Then, in the next imaging frame, the light source unit 20 emits the red light R (S36), the image sensor 48 automatically images the observation object using the red light R, and the image acquisition unit 54 acquires the Rs image that is a final image required for the correction of the oxygen saturation observation mode (S37).

As described above, in a case where the plurality of preliminarily captured images (that is, the Bp image, the Bq image, the Gr image, and the Rs image) required for the correction of the oxygen saturation observation mode are acquired while generation and a display of the white light image 202 are inserted, the correction information calculation unit 75 calculates the biological information peculiar to the observation object showing the part, state, and the like of the observation object as the correction information using these preliminarily captured images (S38). In a case where the correction information calculation unit 75 calculates the correction information, the compensation amount calculation unit 76 corrects the oxygen saturation observation mode by compensating for the correlation to be used for the calculation of the oxygen saturation using the correction information calculated the correction information calculation unit 75 (S40).

Figure 13:
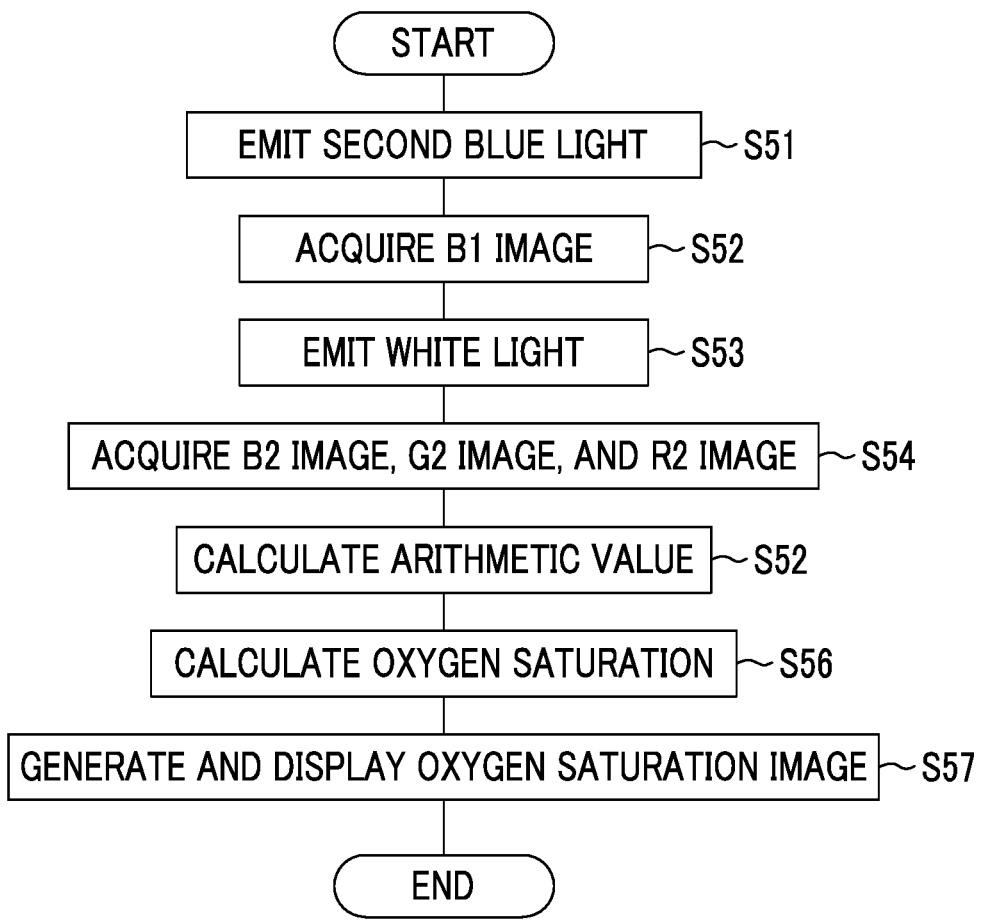
FIG. 13 is a flowchart illustrating a flow of the operation of the oxygen saturation observation mode (biological information observation mode).

As illustrated in FIG. 13, in the oxygen saturation observation mode (Step S13 of FIG. 11), the light source unit 20 first emits the second blue light BL (S51). The, then image sensor 48 automatically images the observation object using the second blue light BL, and the image acquisition unit 54 acquires the B1 image indispensable for the calculation of the oxygen saturation (S52). Thereafter, in the next imaging frame, the light source unit 20 emits the white light (S53), the image sensor 48 automatically images the observation object using the white light, and thereby the image acquisition unit 54 acquires the B2 image the G2 image, and the R2 image required for the calculation of the oxygen saturation and the generation of the oxygen saturation image (S54).

In a case where the B1 image, the B2 image, the G2 image, and the R2 image are obtained in this way, the arithmetic value calculation unit 70 calculates arithmetic values required for the calculation of the oxygen saturation (S55). Specifically, the arithmetic value calculation unit 70 calculates the ratio B1/G2 and the ratio R2/G2, respectively, for each pixel.

Then, the biological information calculation unit 72 refers to the correlation of the data storage unit 71, and calculates the oxygen saturation of the observation object for each pixel from the ratio B1/G2 and the ratio R2/G2 calculated by the arithmetic value calculation unit 70 (S56). Though natural, the biological information calculation unit 72 does not use the default correlation stored in advance in the data storage unit 71 but uses the correlation compensated for by the correction unit 77 in the correction mode. For this reason, since there is no influence from the error factor peculiar to the observation object, the oxygen saturation calculated by the biological information calculation unit 72 is accurate.

In a case where the biological information calculation unit 72 calculates the oxygen saturation, the image generation unit 73 gives a gain according to the oxygen saturation to the B2 image, the G2 image, and the R2 image, and generates the oxygen saturation image representing the values of the oxygen saturation using the pseudo-colors, and the display control unit 66 displays the oxygen saturation image on the monitor 18 (S57).

As described above, the endoscope system 10 has the biological information observation mode, the correction mode in which the biological information observation mode is corrected. In the correction mode, the endoscope system 10 not only simply obtain the preliminarily captured images to correct the biological information observation mode, but also generates and displays the white light image 202 while (or before or after) the preliminarily captured images are obtained. For this reason, the doctor or the like can continue observing the observation object even during the correction mode.

Moreover, since the white light image 202 to be displayed on the monitor 18 during the correction mode is acquired substantially simultaneously with the preliminarily captured images, this white light image represents the state of the observation object while, before, or after the preliminarily captured images are obtained. For this reason, the doctor or the like obtains an opportunity to determine whether or not the preliminary capturing has been appropriately performed or whether or not the oxygen saturation observation mode that is the biological information observation mode has been accurately corrected, by the display of the white light image 202 during the correction mode.

In a case where the oxygen saturation observation mode (biological information observation mode) is executed in a case where the preliminary capturing fails in the correction mode that is automatically performed at the time of switching to the special observation mode and the correction is not accurate, it is natural that the oxygen saturation is inaccurate. Thus, the oxygen saturation image cannot be utilized for diagnosis. In contrast, in the endoscope system 10, there is an opportunity to determine whether or not the correction has been appropriately performed by displaying the white light image 202 during the correction mode. Thus, as needed, before the process proceeds to the oxygen saturation observation mode, the correction mode can be executed again to reliably and accurately correct the oxygen saturation observation mode. Hence, in the endoscope system 10, in a case where there is no change (for example, secretion of mucus, or the like) of the observation object in which the correction is required again, the oxygen saturation can be reliably and accurately calculated in a case where the process has proceeded to the oxygen saturation observation mode.

In addition, in the above first embodiment, the compensation amount calculation unit 76 calculates the compensation amount ΔD using the second feature space, but may also calculate the compensation amount ΔD by performing conversion processing, in which the matrix processing and a one-dimensional look-up table (1D-LUT) are combined with each other, on the Bp image, the Bq image, the Gr image, and the Rs image.

In the above first embodiment, the oxygen saturation observation mode is corrected with respect to the adhesion amount or concentration of the yellow coloring agent. However, the oxygen saturation observation mode may be corrected with respect to states peculiar to other observation objects. In this case, the correction information calculation unit 75 may calculate biological information regarding a state or the like peculiar to an observation object used as a correction target, the like as the correction information, instead of the biological information regarding the adhesion amount or concentration of the yellow coloring agent. The operation of the compensation amount calculation unit 76 and the correction unit 77 is the same as that of the above first embodiment.

In the correction mode of the above first embodiment, in order to obtain the preliminarily captured images, all the white lights are emitted to obtain the white light images 202 while the first blue light BS, the second blue light BL, the green light G, and the red light R are emitted (refer to FIG. 4). However, any of the timings at which these white lights are emitted can be omitted. Additionally, the white light may be emitted to obtain the white light image 202 before emission of the first blue light BS, or the white light may be emitted to obtain the white light image 202 also after emission of the red light R. That is, during the correction mode, the white light may be emitted at least once to generate and display the white light image 202.

In the correction mode of the above first embodiment, except for the white light image 202, the preliminarily captured images are acquired in order of the Bp image, the Bq image, the Gr image, and the Rs image (refer to FIG. 12). However, any acquisition order of the preliminarily captured images may be adopted. For example, the preliminarily captured images may be acquired in order of the Rs image, the Bq image, the Bp image, and the Gr image. However, in a case where there is deviation (movement) of the observation object in the Bp image and the Bq image among these preliminarily captured images, the correction accuracy of the oxygen saturation observation mode is particularly apt to decrease. For this reason, it is preferable that the Bp image and the Bq image are continuously acquired as much as possible. That is, it is preferable that the light emission interval of two correction illumination lights of a combination that most contributes to the calculation accuracy of the compensation amount ΔD to be used for the correction of the oxygen saturation observation mode among a plurality of correction illumination lights can be made shorter than the light emission interval of the other correction illumination lights. It is needless to say that the Bp image and the Bq image are continuously acquired thoroughly with respect to the acquisition order of the preliminarily captured images, and an imaging frame for generating and displaying the white light image 202 may be inserted between the Bq image and the Bq image.

Second Embodiment

Figure 14:
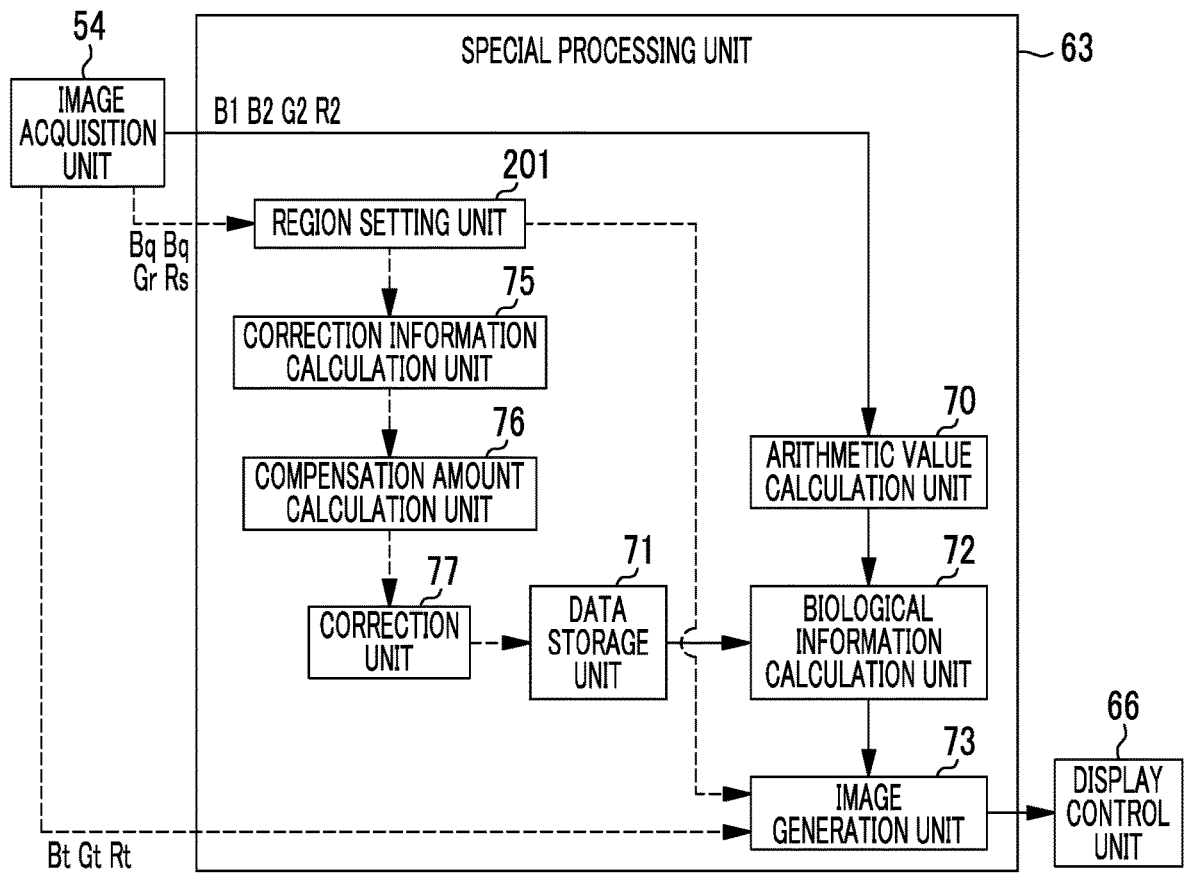
FIG. 14 is a block diagram of a special processing unit of a second embodiment.

In the first embodiment, the biological information observation mode (oxygen saturation observation mode) are corrected using an entire preliminarily captured image. However, the biological information observation mode may be corrected using only a portion of the preliminarily captured image instead of the entire preliminarily captured image. In a case where the biological information observation mode is corrected using a portion of the preliminarily captured image in this way, as illustrated in FIG. 14, the special processing unit 63 is provided with a region setting unit 201 that operates in the correction mode.

The region setting unit 201 acquires preliminarily captured images (that is, the Bp image, the Bq image, the Gr image, and the Rs image), to be used for the correction of the oxygen saturation observation mode that is the biological information observation mode, from the image acquisition unit 54, and sets a portion of each of these preliminarily captured images to a region (hereinafter referred to as a use region) 203 (refer to FIG. 15) to be used for the connection of the oxygen saturation observation mode. In a case where the region setting unit 201 sets the use region 203 with respect to the preliminarily captured image, the correction information calculation unit 75 calculates correction information only on the use region 203 set by the region setting unit 201. Accordingly, since the compensation amount calculation unit 76 also calculates the compensation amount ΔD with respect to the use region, only the use region 203 that is a portion of the preliminarily captured image instead of the entire preliminarily captured image is used for the compensation (that is, the correction of the oxygen saturation observation mode) of the correlation performed by the correction unit 77. In this way, in a case where the use region 203 is set in a portion of the preliminarily captured image and the oxygen saturation observation mode is corrected using only the use region 203 instead of the entire preliminarily captured image, the error factor of the correction can be reduced. Thus, the oxygen saturation observation mode can be more accurately corrected.

The region setting unit 201 detects, for example, portions that become the error factor of the correction, such as an excessively bright portion (a portion in which halation occur), an excessively dark portion (a portion that is crushed black due to shortage of the quantity of light), and a portion to which residual substances or residual liquid adheres, from the preliminarily captured image, and sets regions excluding these portions to the use region 203. The region setting unit 201 may also perform determination from the shape or the like of the observation object, detect a normal part that can be said not to have a lesion or the like, and set the detected normal part to the use region 203. Additionally, the region setting unit 201 may set a region excluding a circumferential edge of an image in which the illuminance unevenness occurs easily, and a certain range of an inner portion of the observation object to the use region 203. In addition, the use region 203 can also be manually set by an operation input from the console 19 or the like.

Figure 15:
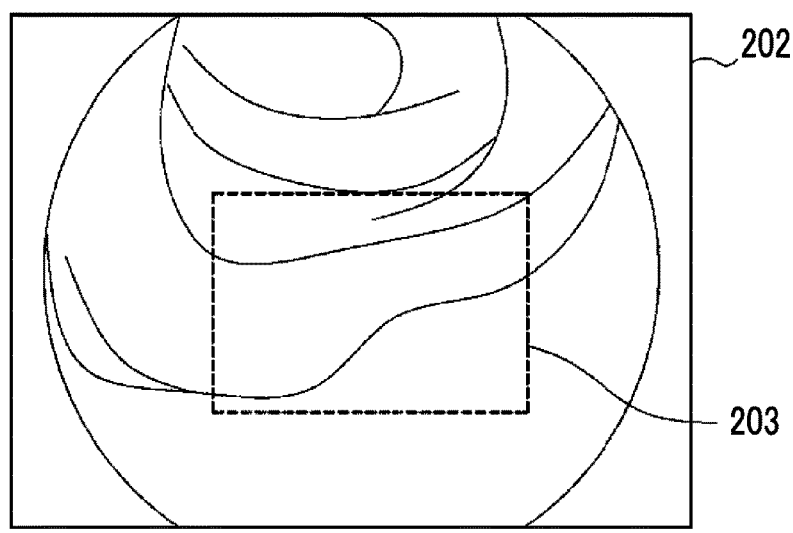
FIG. 15 is a white light image in which a use region is overlappingly displayed.

As described above, in a case where the region setting unit 201 sets a portion of a preliminarily captured image to the use region 203 and uses only the use region 203 for the correction of the oxygen saturation observation mode, the image generation unit 73 acquires information on the position and range of the use region 203 (hereinafter referred to as positional information) set by the region setting unit 201, from the region setting unit 201. For example, as illustrated in FIG. 15, in a case where the display control unit 66 displays the white light image 202 on the monitor 18, the display control unit 66 overlappingly display the use region 203 set by the region setting unit 201 on the white light image 202 on the basis of the positional information.

In a case where the use region 203 is overlapping displayed on the white light image 202 in this way, which region has been used for the correction of the oxygen saturation observation mode can be visually recognized. Hence, the doctor or the like can confirm whether or not the use region 203 is unsuitable in addition to confirming whether or not the use region 203 is in a state that may become an error factor, such as the movement of the observation object using the white light image 202, and can perform the correction of the oxygen saturation again in a case where the use region 203 set by the region setting unit 201 set is unsuitable.

In the above second embodiment, the region setting unit 201 detects and sets the use region 203 using the preliminarily captured image. Instead of this, however, the region setting unit 201 may set the use region 203 using the white light image 202.

In the above second embodiment, the use region 203 is overlapping displayed on the white light image 202. However, a numerical value of the compensation amount ΔD or an indicator showing the numerical value of the compensation amount ΔD may be further overlappingly displayed on the white light image 202. This is because specific numerical values of the compensation amount ΔD also become a determination material of whether or not the correction of the oxygen saturation observation mode has been accurately performed. For example, in a case where the compensation amount ΔD is extremely large, there is a possibility that the state of the observation object is far from a normal state to such a degree that a lesion is spreading in an imaged entire location. Such an abnormality can be perceived in a case where the specific numerical values of the compensation amount ΔD are viewed. The overlap display of the numerical values of the compensation amount ΔD are effective also in the case of the first embodiment.

Third Embodiment

In the first embodiment, in the correction mode, the light source unit 20 inserts the emission of the white light two or more times while sequentially emitting the correction illumination lights for obtaining preliminarily captured images. Accordingly, the white light images 202 are respectively generated and displayed on the monitor 18 from the images obtained in the respective imaging frames in which the white light is emitted.

Figure 16:
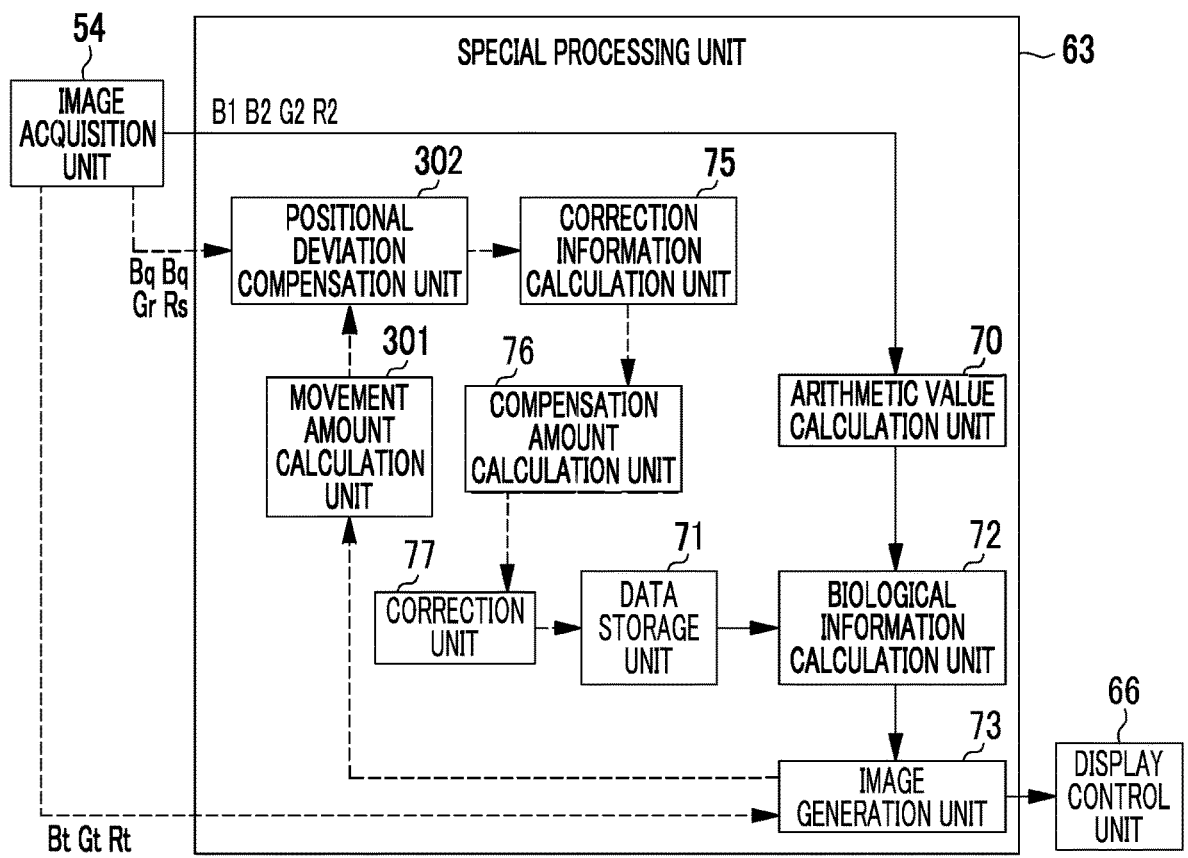
FIG. 16 is a block diagram of a special processing unit of a third embodiment.

In this way, in the correction mode, in a case where the light source unit 20 inserts the emission of the white light two or more times while sequentially emitting the correction illumination lights for obtaining the preliminarily captured images, and obtains the plurality of white light image 202, as illustrated in FIG. 16, it is preferable that the special processing unit 63 is further provided with the movement amount calculation unit 301 and a positional deviation compensation unit 302 that operate in the correction mode.

The movement amount calculation unit 301 sequentially acquires the white light images 202 generated by the image generation unit 73, and calculates the movement amount of the observation object from the plurality of acquired white light images 202. Specifically, through matching of two white light images 202 that are sequentially acquired, the movement amount calculation unit 301 detects a plurality of vectors (henceforth, movement vector) showing the movement of the observation object between the white light images 202. Directions and sizes, such as the movement, rotation, and deformation of the observation object are calculated from these movement vectors. Directions and sizes, such as the movement, rotation, and deformation of the observation object that are calculated in this way are the movement amount.

The positional deviation compensation unit 302 compensates for the positional deviation of the observation object of the correction images using the movement amount calculated by the movement amount calculation unit 301. That is, the positional deviation compensation unit 302 compensates for the positional deviation of the observation object of the Bp image, the Bq image, the Gr image, and the Rs image that are the correction images.

For example, in a case where a movement amount is calculated from the white light image 202 (the white light image 202 obtained in Step S25 of FIG. 12) first obtained in the correction mode, and the white light image 202 (the white light image 202 obtained in Step S30 of FIG. 12) that is obtained next, this movement amount is approximately equal to the movement amount of the observation object between Bp images, Bq images, or Gr images that are acquired before and after the white light image 202 that is first obtained and the white light image 202 that is next obtained. Similarly, in a case where a movement amount is calculated from the white light image 202 (the white light image 202 obtained in Step S30 of FIG. 12) that is secondly obtained in the correction mode, and the white light image 202 (the white light image 202 obtained in Step S35 of FIG. 12) that is thirdly obtained, this movement amount is approximately equal to the movement amount of the observation object between Bq images, Gr images, or Rs images that are acquired before and after these images. Hence, in a case where these movement amounts are used, even though there is a slight movement in the observation object of each of the Bp image, the Bq image, the Gr image, and the Rs image, the positional deviation of the observation object between these images can be compensated for.

The correction information calculation unit 75 calculates the correction information using the Bp image, the Bq image, the Gr image, and the Rs image obtained by compensating for the positional deviation of the observation object using the positional deviation compensation unit 302 as described above. For this reason, the correction information can be more accurately calculated than in a case where the positional deviation of the observation object is not compensated for. Hence, in the present embodiment, since an error resulting from the movement of the observation object can be reduced, the correction of the oxygen saturation observation mode becomes more accurate.

In addition, in the above third embodiment, the movement amount calculation unit 301 calculates the movement amount using the white light images 202 generated by the image generation unit 73. However, the movement amount calculation unit 301 may calculate the movement amount using images for generating the white light images 202, instead of the white light images 202. Specifically, since the image generation unit 73 generates the white light images 202 using the Bt image, the Gt image, and the Rt image, the movement amount calculation unit 301 may calculate the movement amount using any one or all of the Bt image, the Gt image and the Rt image.

Fourth Embodiment

In the above third embodiment, in the correction mode, the movement amount is calculated from the plurality of white light images 202, and the positional deviation of the observation object of the correction images is compensated for. Instead of this, however, a light quantity ratio of the plurality of white light images 202 may be calculated, and a light quantity ratio of the correction images may be compensated for using the calculated light quantity ratio.

Figure 17:
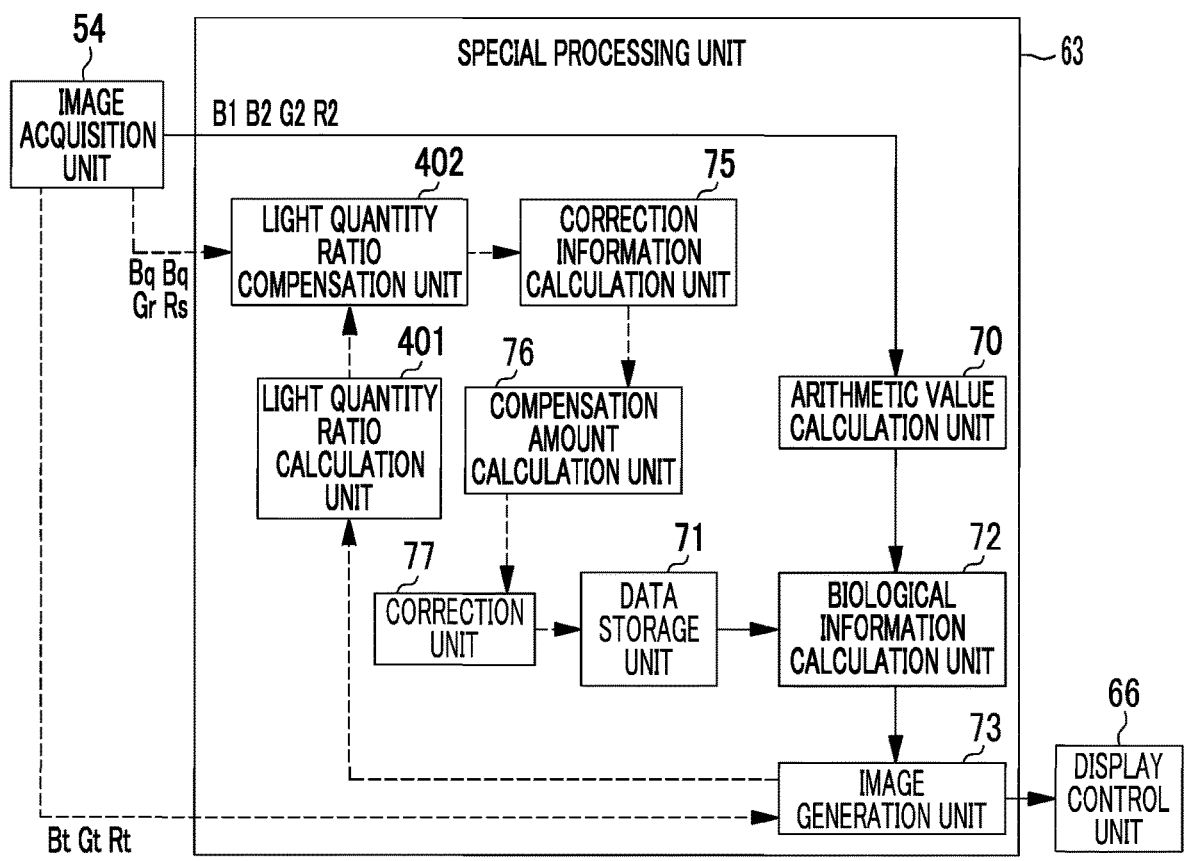
FIG. 17 is a block diagram of a special processing unit of a fourth embodiment.

In this case, as illustrated in FIG. 17, the special processing unit 63 are provided with a light quantity ratio calculation unit 401 and a light quantity ratio compensation unit 402 that function in the correction mode. The light quantity ratio calculation unit 401 sequentially acquires the white light images 202 from the image generation unit 73, and calculates the light quantity ratio of the white light images 202. The light quantity of the images is, for example, an average value (hereinafter referred to as average luminance) of the luminances of all the pixels or some pixels, and the light quantity ratio of the images is a ratio of the average luminances of images to be compared with each other. Hence, the light quantity ratio of the plurality of white light images 202 is a ratio of the average luminances of the respective white light images 202.

The light quantity ratio compensation unit 402 compensates for the light quantity ratio of the correction images using the light quantity ratio calculated by the light quantity ratio calculation unit 401. For example, in a case where the light quantity ratio calculation unit 401 calculates a light quantity ratio between the white light image 202 (the white light image 202 obtained in Step S25 of FIG. 12) that is first obtained in the correction mode, and the white light image 202 (the white light image 202 obtained in Step S30 of FIG. 12) that is next obtained, the light quantity ratio represents approximately a change in the quantity of light between Bp images, Bq images, or Gr images that are acquired before and after the white light images 202. Additionally, in a case where the light quantity ratio calculation unit 401 calculates a light quantity ratio between the white light image 202 (the white light image 202 obtained in Step S30 of FIG. 12) that is secondly obtained in the correction mode, and the white light image 202 (the white light image 202 obtained in Step S35 of FIG. 12) that is thirdly obtained, the light quantity ratio represents approximately a change in the quantity of light between Bq images, Gr images, or Rs images that are acquired before and after these white light images 202. Hence, the light quantity ratio compensation unit 402 can compensate for the light quantity ratios of the Bp image, the Bq image, the Gr image, and the Rs image by using these light quantity ratios.

Then, the correction information calculation unit 75 calculates the correction information using the Bp image the Bq image, the Gr image, and the Rs image obtained by compensating for the light quantity ratios using the light quantity ratio compensation unit 402, as described above. For this reason, even though there are changes in the quantity of light between the Bp image, the Bq image, the Gr image, and the Rs image because there are variations in light emission amount between the first blue light BS, the second blue light BL, the green light G, and the red light R that are the illumination light, the light quantity ratio of these respective correction images is compensated for. Thus, in the present embodiment, the correction information can be accurately calculated. Hence, in the present embodiment, since an error resulting from the changes in the quantity of light between the correction images can be reduced, the correction of the oxygen saturation observation mode becomes more accurate.

In addition, in the above fourth embodiment, the light quantity ratio calculation unit 401 calculates the light quantity ratio using the white light images 202 generated by the image generation unit 73. However, the light quantity ratio calculation unit 401 may calculate the light quantity ratio using images for generating the white light images 202, instead of the white light images 202. Specifically, since the image generation unit 73 generates the white light images 202 using the Bt image, the Gt image, and the Rt image, the light quantity ratio calculation unit 401 may calculate the light quantity ratio using any one or all of the Bt image, the Gt image and the Rt image.

In addition, the above fourth embodiment may also be combined with the third embodiment. That is, the movement amount and the light quantity ratio may be calculated from the plurality of white light images 202 obtained in the correction mode, the positional deviation of the observation object of the correction images may be compensated for using these, and the light quantity ratio of the correction images may be compensated for. In this case, the movement amount calculation unit 301 and the positional deviation compensation unit 302 of the third embodiment, and the light quantity ratio calculation unit 401 and the light quantity ratio compensation unit 402 of the fourth embodiment in the special processing unit 63 may be provided.

Fifth Embodiment

Figure 18:
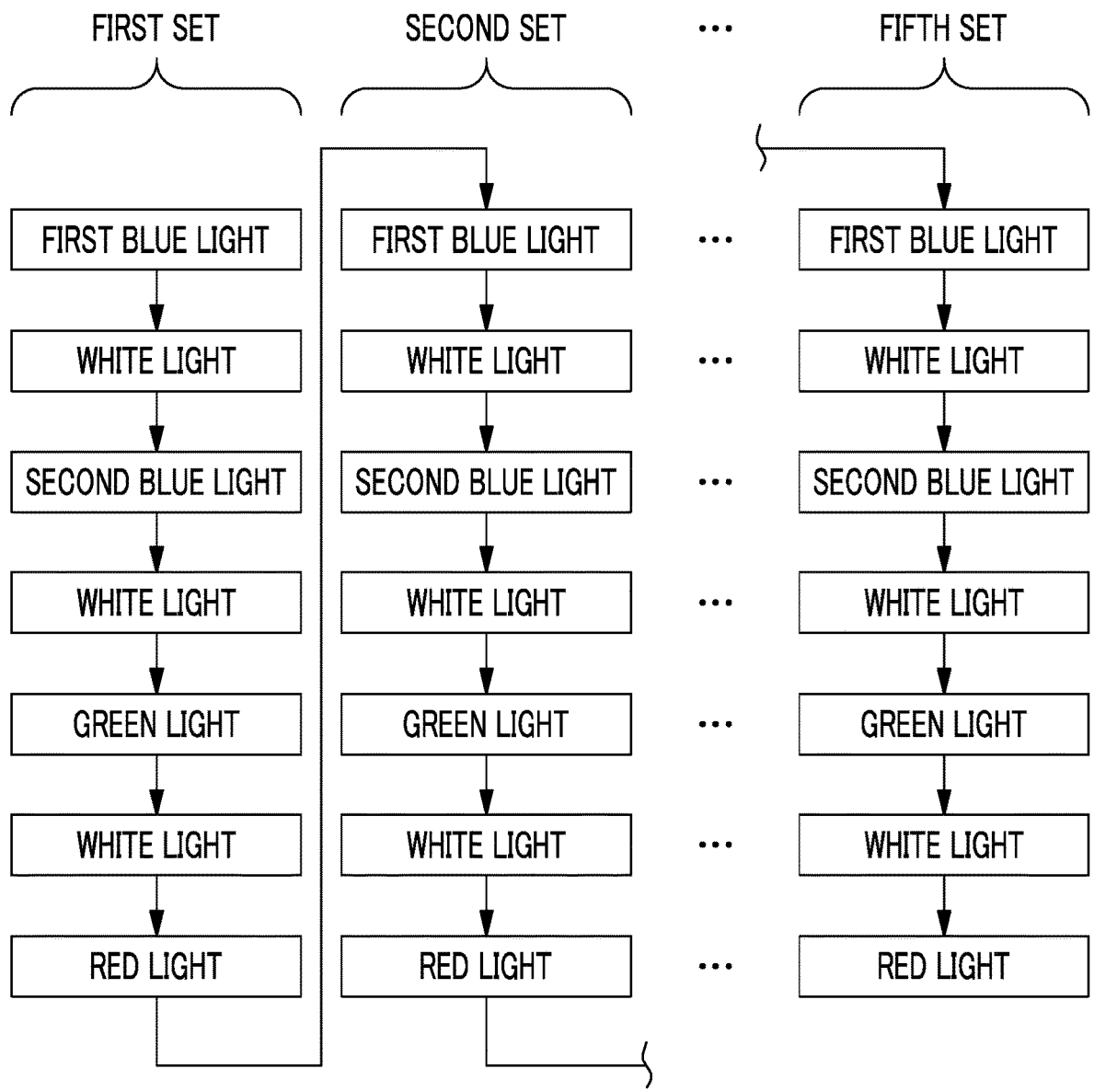
FIG. 18 is a light emission pattern in a correction mode of a fifth embodiment.

In the correction modes of the above first to fourth embodiments, one set of correction images (one set of the Bp image, the Bq image, the Gr image, and the Rs image) are acquired to correct the oxygen saturation observation mode. However, in the correction modes, a plurality of sets of the correction images may be obtained. For example, as illustrated in FIG. 18, similar to the first embodiment, the first blue light BS, the white light, the second blue light BL, the green light G, and the red light R may be defined as one set, and for example, a first set to a fifth set can be collectively executed. Images obtained at the time of emission of the respective lights are the same as those of the first embodiment. Thus, in a case where the correction images only are described, the Bp image, the Bq image, the Gr image, and the Rs image are defined as one set and five sets of the correction images are obtained.

In this way, in a case where the correction images equivalent to the plurality of sets are obtained in the correction mode, a plurality of the compensation amounts ΔD can be calculated by using some correction images among these correction images and changing the combination of correction images to be used. In a case where the correction images equivalent to the above five sets are obtained, the compensation amount calculation unit 76 is able to use at least the correction information calculated using the first set of correction images, thereby calculating a first-set compensation amount (hereinafter referred to as a compensation amount ΔD1 for the purpose of distinction; the same also applies to the other sets) resulting from the first set of correction images. Similarly, a second-set of compensation amount ΔD2, a third-set compensation amount ΔD3, a fourth-set compensation amount ΔD4, and a fifth-set compensation amount ΔD5 may be calculated.

For example, in a case where the average value of the above compensation amounts ΔD1 to ΔD5 is set to the compensation amount ΔD of the above first embodiment, an error resulting from variations or the like in data can be reduced, and the compensation amount ΔD that is still more accurate than the above first embodiment can be calculated. Hence, the oxygen saturation observation mode can be more accurately corrected by obtaining the correction images equivalent to a plurality of sets in the correction mode as in the present embodiment.

In addition, in the above fifth embodiment, the compensation amounts ΔD1 to ΔD5 are calculated for the above sets, respectively. However, compensation amounts may also be calculated by using correction images obtained in different sets in combinations. For example, compensation amounts ΔD may be calculated using the Bq image, the Gr image, the Rs image that are obtained in the first set and the Bp image obtained in the second set. Additionally, compensation amounts may be calculated using the Gr image and the Rs image that are obtained in the first set, and the Bp image and the Bq image that are obtained in the second set. Similarly, twelve compensation amounts ΔD in total may be calculated by changing correction images to be used for two imaging frames. In this way, in a case where five or more compensation amounts ΔD also including the compensation amounts ΔD calculated by combining the correction images obtained in different sets together are averaged, the averaged compensation amount ΔD becomes a value that is still more accurate than that of the above fifth embodiment. Hence, as a result, the oxygen saturation observation mode can be still more accurately corrected.

Additionally, in the above fifth embodiment and modification examples, after the plurality of compensation amounts ΔD are calculated in the correction mode, these compensation amounts are averaged. However, instead of this averaging, a median value or the like of the plurality of compensation amounts ΔD, may be the compensation amount ΔD to be used by the correction unit 77.

Figure 19:
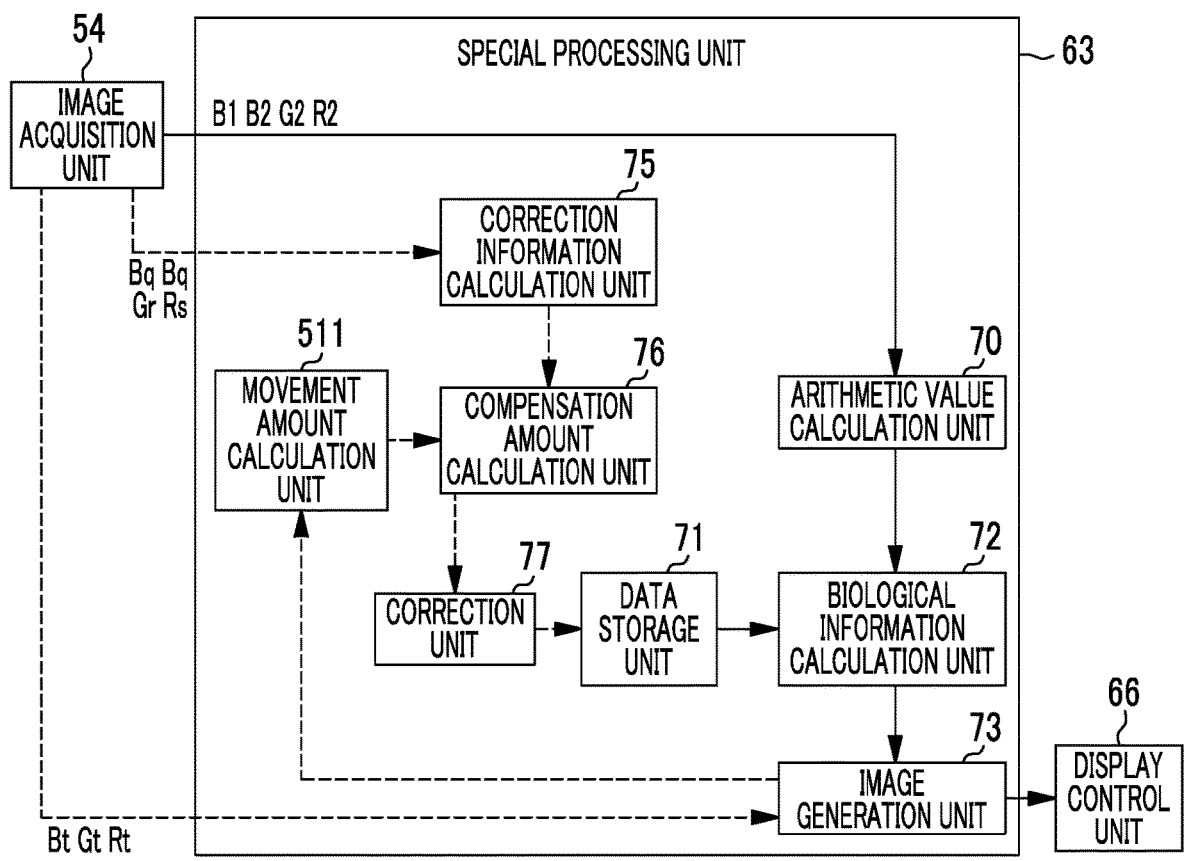
FIG. 19 is a block diagram of a special processing unit of a modification example.

As in the above fifth embodiment, in a case where the plurality of compensation amounts Δ are calculated by acquiring the correction images equivalent to the plurality of sets in the correction mode, as illustrated in FIG. 19, it is preferable that the special processing unit 63 is further provided with a movement amount calculation unit 511. Similar to the movement amount calculation unit 301 of the third embodiment, the movement amount calculation unit 511 sequentially acquires the white light images 202 from the image generation unit 73, and calculates the movement amounts of the observation object between the plurality of acquired white light images 202. However, the movement amount calculation unit 511 inputs the calculated movement amount to the compensation amount calculation unit 76.

Then, in the compensation amount calculation unit 76, as in the above fifth embodiment, the plurality of compensation amounts ΔD are calculated, and a value obtained by weighting and averaging the plurality of compensation amounts ΔD using the movement amount, is set to the compensation amount ΔD to be used in the correction unit 77. For example, in a case where the five compensation amounts ΔD1 to ΔD5 are calculated for the above sets, respectively, and respective movement amounts of the first to fifth sets (or average values of the movement amounts of the respective sets) are α1 to α5, respectively, the compensation amount calculation unit 76 multiplies the compensation amounts ΔD1 to ΔD5 of the respective sets by these movement amounts α1 to α5, respectively to average the results, and calculates the compensation amount ΔD to be used in the correction unit 77. In this way, in a case where the correction unit 77 compensates for the correlation using a value obtained by performing weighting and averaging using the movement amounts, the oxygen saturation observation mode can be still more accurately corrected than the above fifth embodiment.

Additionally, instead of performing weighting and averaging using the movement amount as described above to average the plurality of compensation amounts ΔD, the compensation amount calculation unit 76 may select the compensation amount ΔD optimal for the correction of the oxygen saturation observation mode from the plurality of compensation amounts ΔD using the movement amount. For example, in a case where the five compensation amounts ΔD1 to ΔD5 are calculated for the above sets, respectively, the respective movement amounts of the first to fifth sets (or average values of the movement amounts of the respective sets) are α1 to α5, respectively, and the movement amount α3 of the third set among these movement amounts α1 to α5 is the minimum, the compensation amount calculation unit 76 selects the third-set compensation amount ΔD3 as the compensation amount ΔD to be used by the correction unit 77. In this way, in a case where the compensation amount ΔD of a set with the smallest movement amount or the compensation amount ΔD calculated using the correction images of a combination with the smallest movement amount is selected and is used for the compensation of the oxygen saturation observation mode, the oxygen saturation observation mode can be corrected more easily than a case where the weighted averaging is performed and more accurately than in the fifth embodiment.

Figure 20:
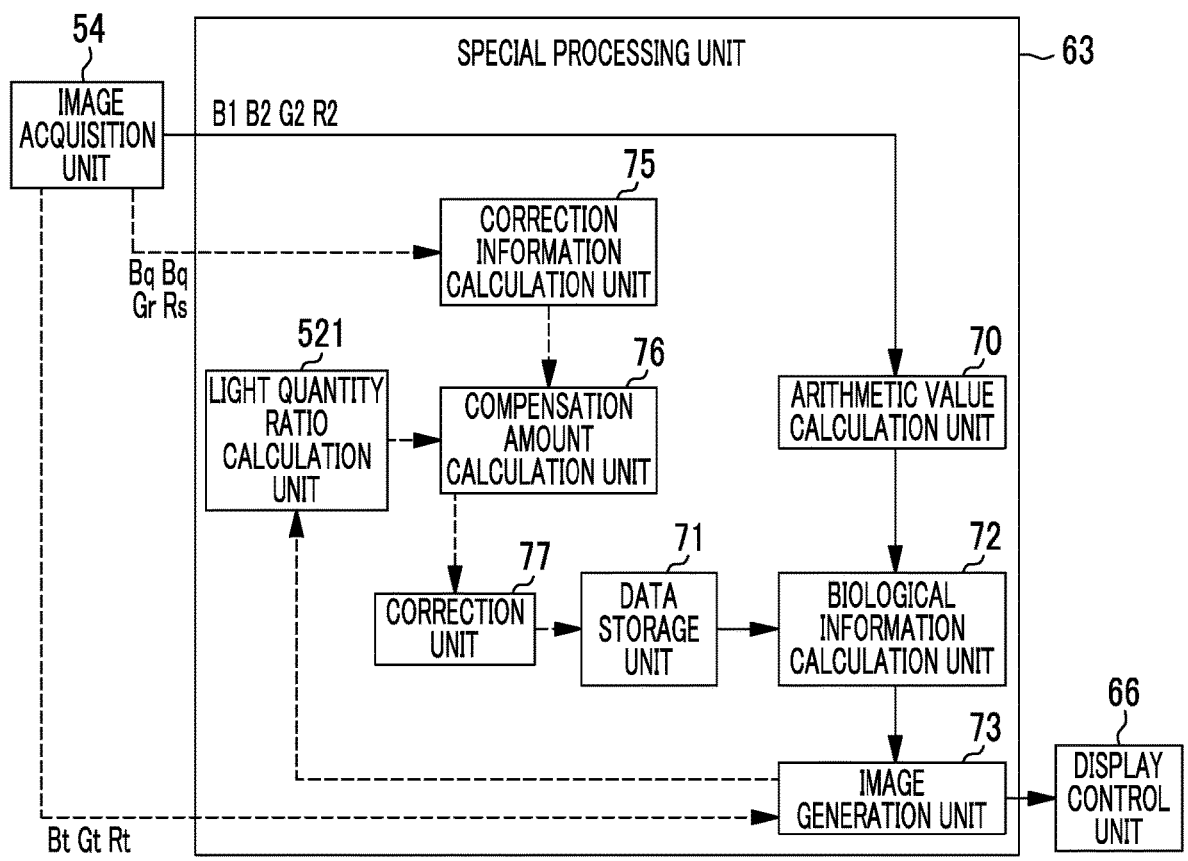
FIG. 20 is a block diagram of the special processing unit of the modification example.

As illustrated in FIG. 20, instead of the movement amount calculation unit 511, a light quantity ratio calculation unit 521, which calculates the light quantity ratio of the plurality of white light images 202 may be provided similarly to the fourth embodiment. However, the light quantity ratio calculation unit 521 calculates a plurality of light quantity ratios, for example, for each set. In this case, the light quantity ratios calculated by the light quantity ratio calculation unit 521 may be used instead of the movement amount calculated by the movement amount calculation unit 511. That is, the plurality of compensation amounts ΔD may be weighted and averaged using the light quantity ratios calculated by the light quantity ratio calculation unit 521, and the compensation amount ΔD to be used in the correction unit 77 may be calculated. Additionally, the compensation amount ΔD (for example, the compensation amount ΔD of a set with a minimum light quantity ratio) optimal for the correction of the oxygen saturation observation mode can be selected from the plurality of compensation amounts ΔD using the light quantity ratios calculated by the light quantity ratio calculation unit 521.

In addition, in the above fifth embodiment, how many sets of correction images are to be obtained during the correction mode is determined. Instead of this, however, the time to execute the correction mode may be determined. For example, the duration time of the correction mode may be set to 5 seconds or the like, and correction images may be acquired as many as possible, also including the time to acquire the white light image 202, within this duration time.

In the above first to fifth embodiments, in a case where the observation mode is switched to the special observation mode, the correction mode is automatically executed. However, in a case where the correction mode is not automatically executed and the observation mode is switched to the special observation mode, the oxygen saturation observation mode may be automatically executed, and the correction mode may be randomly executed during the oxygen saturation observation mode.

Figure 21:
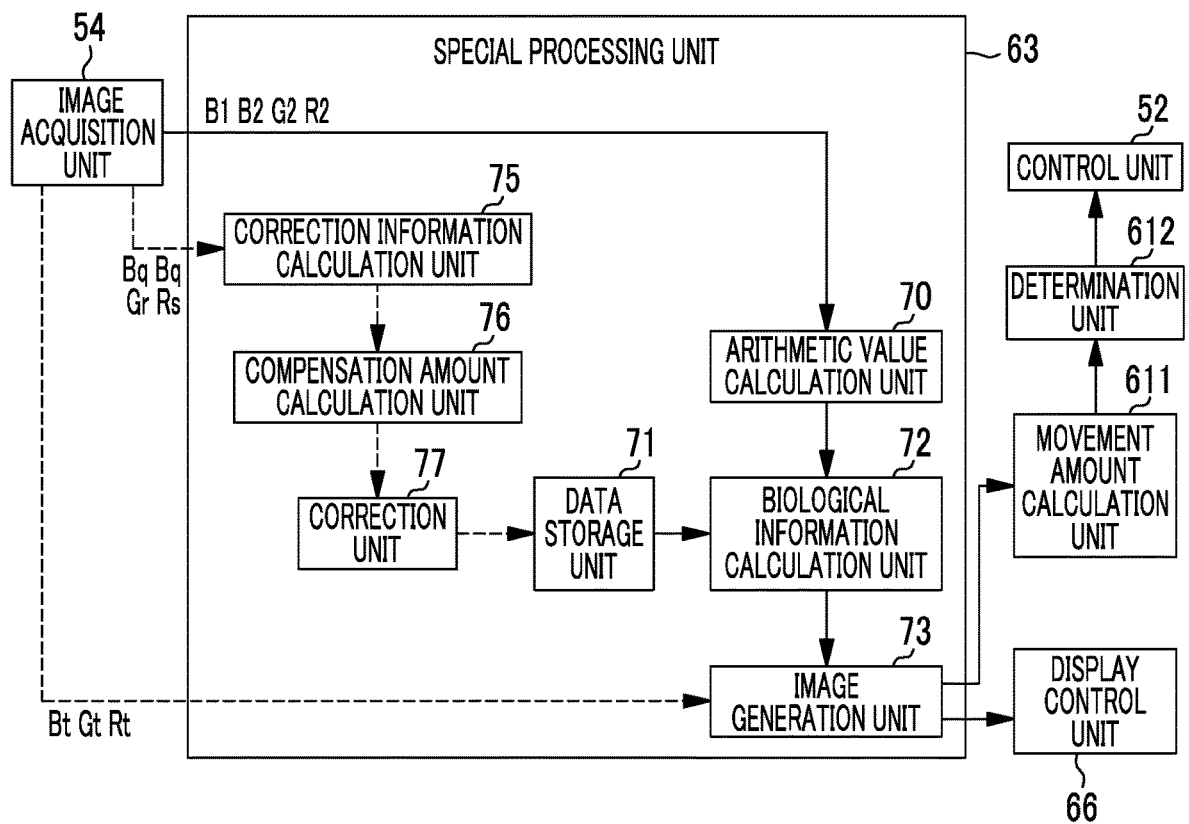
FIG. 21 is a block diagram of the special processing unit and its periphery of the modification example.

For example, as illustrated in FIG. 21, the processor device 16 may be provided with a movement amount calculation unit 611 that sequentially acquires oxygen saturation images to calculate the movement amount, and a determination unit 612 that determines whether or not the correction mode is to be executed using the movement amount calculated by the movement amount calculation unit 611. For example, in a case where the movement amount becomes equal to or less than a threshold value and the movement of the observation object is small, the determination unit 612 determines that the correction mode is executed, and inputting a control signal showing that effect to the control unit 52, thereby automatically inserting the correction mode during the oxygen saturation observation mode. In this way, in a case where a situation optimal for the correction of the oxygen saturation observation mode is determined using the movement amount, and the correction mode is executed in a case where the situation optimal for the correction of the correction mode is brought about, the correction of the oxygen saturation observation mode is apt to succeed.

Although the movement amount calculation unit 611 calculates the movement amount from the oxygen saturation images, the movement amount may be calculated using the images (the B1 image, the B2 image, the G2 image, and the R2 image) for generating the oxygen saturation images instead of the oxygen saturation images. Additionally, in a case where it is determined that the correction mode is executed, the determination unit 612 inputs a control signal to the control unit 52, thereby automatically inserting the correction mode during the oxygen saturation observation mode. Instead of this, however, the fact that the situation is suitable for the correction mode may be notified of using the display (message or the like) of the monitor 18 or the like, and manual switching to the correction mode may be prompted. Additionally, the movement amount calculation unit 611 and the determination unit 612 may be provided at the special processing unit 63.

Figure 22:
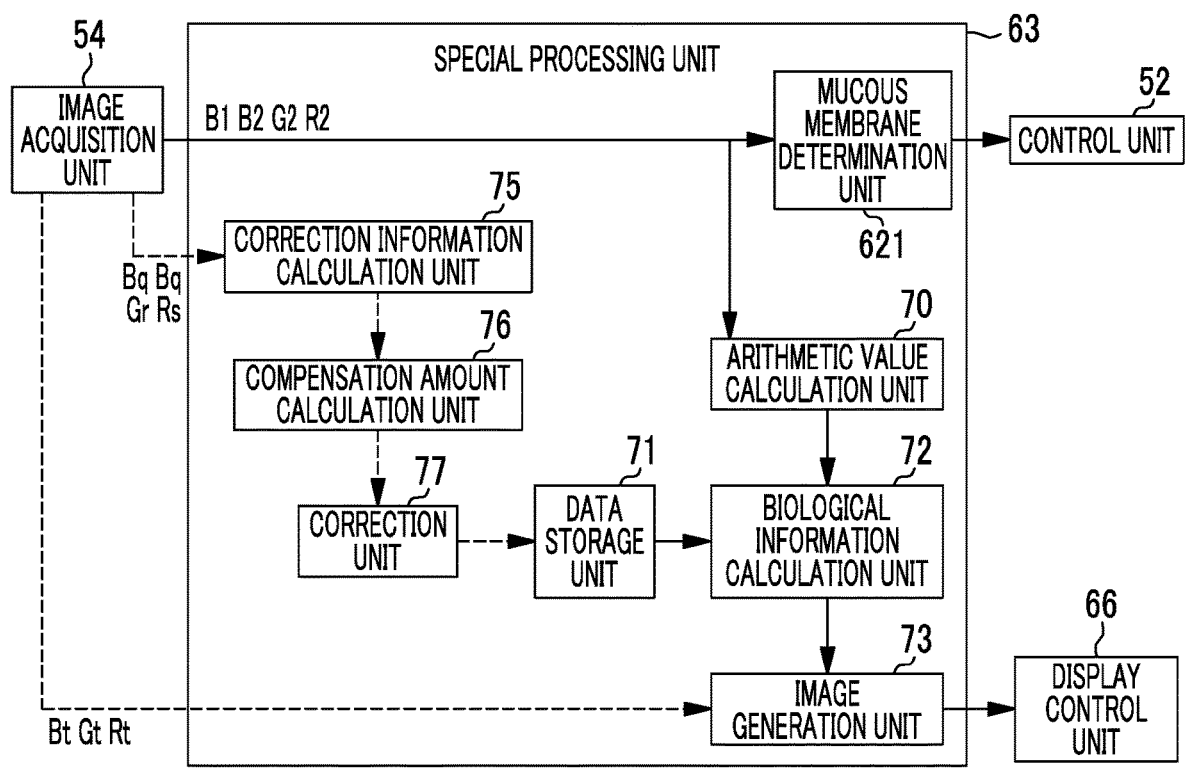
FIG. 22 is a block diagram of the special processing unit of the modification example.

As illustrated in FIG. 22, in a case where the special processing unit 63 is provided with a mucous membrane determination unit 621 that determines the state of a mucous membrane, the correction mode may be inserted during the oxygen saturation observation mode, in accordance with a determination result of the mucous membrane determination unit 621. The mucous membrane determination unit 621, for example, acquires the B1 image, the B2 image, the G2 image, or the R2 image from the image acquisition unit 54, and detects the state of the mucous membrane of the observation object using any one or all of these images. Then, in a case where there is no mutation shape or mutation structure, such as protuberances suspected of a lesion, it is determined that the mucous membrane of the observation object is in a state suitable for the correction mode, and a control signal prompting the execution of the correction mode is input to the control unit 52. Accordingly, the correction mode may be automatically inserted during the oxygen saturation observation mode.

The mucous membrane determination unit 621 may determine the color of the mucous membrane. For example, in a case where there is no discoloration (for example, redness) or the like suspected of a lesion, or in a case where the color of the mucous membrane varies due to the endoscope 12 entering the stomach from the esophagus, or the like, and it is determined that the observation object becomes a different organ, the mucous membrane determination unit 621 is able to input a control signal prompting the execution of the correction mode to the control unit 52, and automatically insert the correction mode during the oxygen saturation observation mode. In addition, also in a case where the mucous membrane determination unit 621 is provided, instead of automatically inserting the correction mode, the fact that the situation is suitable for the correction mode may be notified of using the display (message or the like) of the monitor 18 or the like, and manual switching to the correction mode may be prompted.

Figure 23:
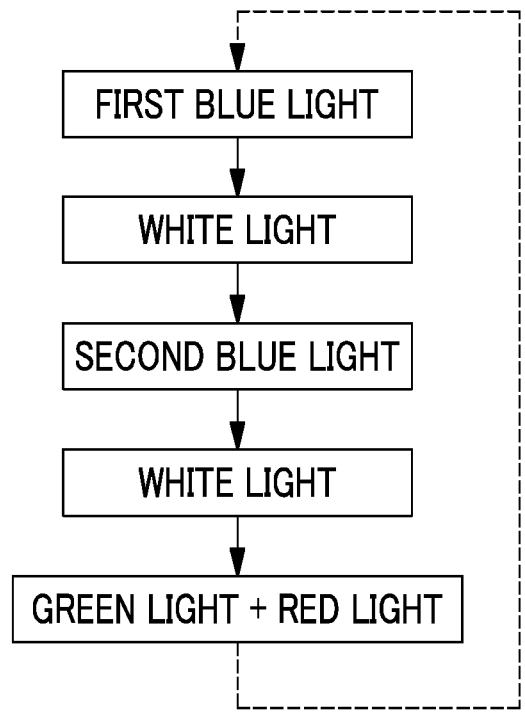
FIG. 23 is a light emission pattern in the correction mode.
Figure 24:
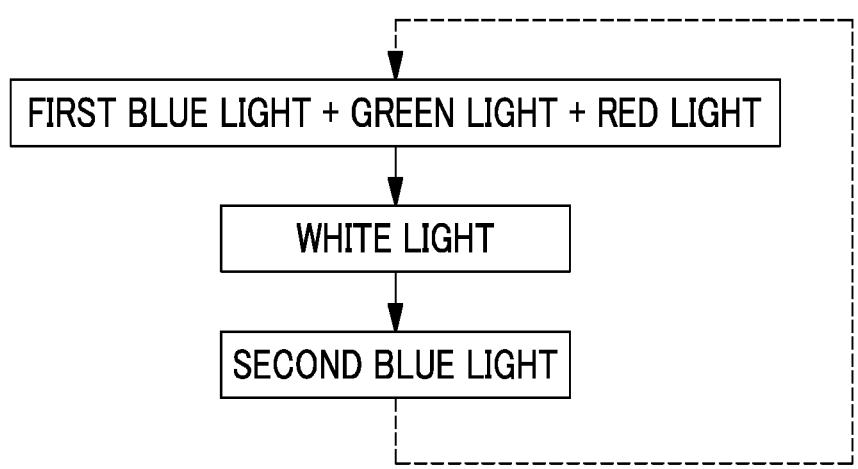
FIG. 24 is a light emission pattern in the correction mode.

In the above first to fifth embodiments, the first blue light BS, the second blue light BL, the green light G, and the red light R are respectively and singly emitted in the correction mode to obtain the correction images. However, some lights may be simultaneously emitted or some correction images may be simultaneously acquired. For example, as illustrated in FIG. 23, the green light G and the red light R may be simultaneously emitted, and the Gr image and the Rs image may be simultaneously acquired. Additionally, as illustrated in FIG. 24, the first blue light BS, the green light G, and the red light R may be simultaneously emitted to simultaneously acquire the Bp image, the Gr image, and the Rs image, and the second blue light BL may be singly emitted to separately acquire the Bq image. Similarly, the first blue light BS may be singly emitted to acquire the Bp image, and the second blue light BL, the green light G, and the red light R may be simultaneously emitted to simultaneously acquire the Bq image, the Gr image, and the Rs image. That is, in a case where the first blue light BS and the second blue light BL to be received in the B pixel are respectively emitted in different imaging frames to separately obtain the Bp image and the Bq image, the other correction images may be simultaneously obtained.

In the above first to fifth embodiments, basically, the oxygen saturation observation mode is corrected in a one-time correction mode. However, in a case where the correction mode is manually or automatically executed two or more times, correction results in a previously executed correction mode may be overlappingly corrected. That is, in a case where the correction mode is executed two or more times, the default correlation always stored in advance in the data storage unit 71 may not be compensated for, but a correlation that is compensated for in the previous correction mode may be compensated for. By doing in this way, even though the correction accuracy in the one-time correction mode is somewhat low, the correction accuracy can be improved stepwise.

In the above first to fifth embodiments, the biological information observation mode is the oxygen saturation observation mode. However, the invention can also be applied to the biological information observation mode in which biological information other than the oxygen saturation is calculated and the like.

In the above first to fifth embodiments, the plurality of correction illumination lights having different colors (wavelength) are used in the correction mode. However, the correction of the biological information observation mode may be performed using a plurality of preliminarily captured images obtained by imaging the observation object two or more times using correction illumination lights having the same color.

Figure 25:
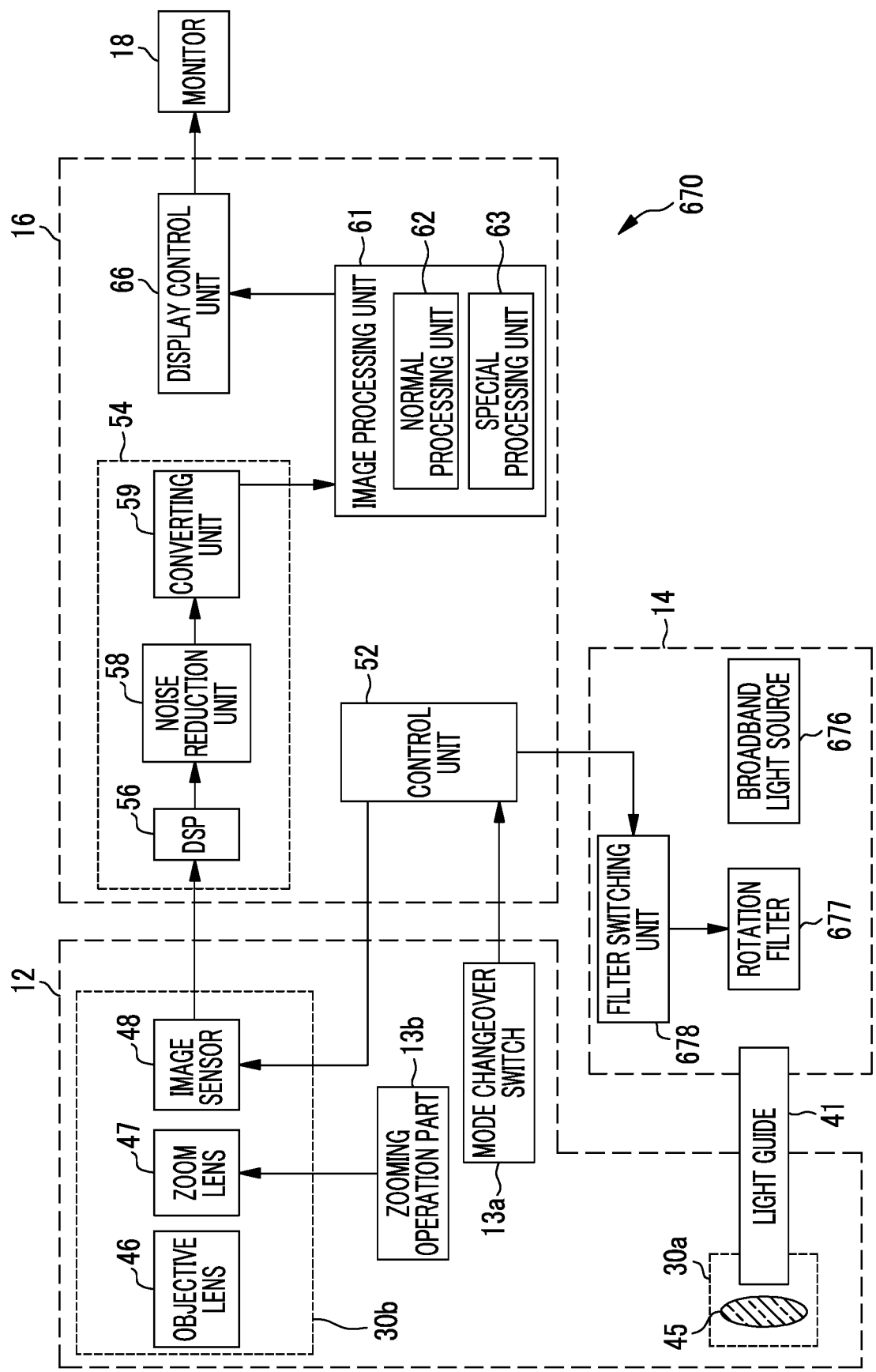
FIG. 25 is a block diagram of an endoscope system using a broadband light source and a rotation filter.

In the above first to fifth embodiments, the light source unit 20 has the plurality of light sources 20a to 20d, and lights emitted by these light sources are overlapped with each other to form the illumination light. However, the light source unit 20 may form the illumination light by extracting and using some components from the light emitted by a broadband light source. For example, in an endoscope system 670 illustrated in FIG. 25, the light source unit 20 is provided with a broadband light source 676, a rotation filter 677, and a filter switching unit 678 instead of the respective light sources 20a to 20d and the light source control unit 22 of the first embodiment. Additionally, in the endoscope system 670, the image sensor 48 is a monochrome sensor in which the color filter is not provided. The others are the same as those of the endoscope system of the first embodiment.

The broadband light source 676 is a xenon lamp, a white LED, or the like, and emits the white light of which the wavelength range ranges from blue to red. The rotation filter 677 is rotatably disposed on a light path of the broadband light source 676, limits the range of the white light emitted by the broadband light source 676, and some components of the white light are incident on the light guide 41 as the illumination light.

Figure 26:
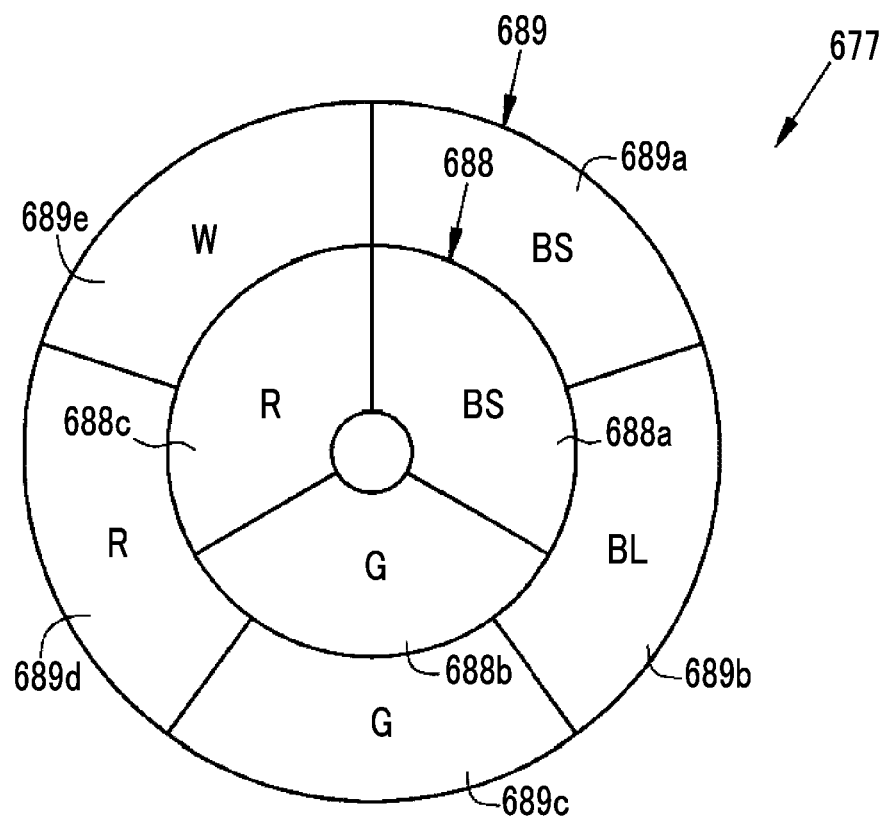
FIG. 26 is an explanatory view illustrating the configuration of the rotation filter.

As illustrated in FIG. 26, the rotation filter 677 is circular and has band limiting filters, respectively, at an inner periphery and an outer periphery thereof. A band limiting filter (hereinafter referred to as an inner filter) 688 at the inner periphery are divided into four compartments in the circumferential direction, and each compartment is provided with a BS filter 688a through which the first blue light BS is transmitted, a G filter 688b through which the green light G is transmitted, and an R filter 688c through which the red light R is transmitted. A band limiting filter (hereinafter referred to as an outer filter) 689 at the outer periphery are divided into five compartments in the circumferential direction, and each compartment is provided with a BS filter 689a through which the first blue light is transmitted, a BL filter 689b through which the second blue light BL is transmitted, a G filter 689c through which the green light G is transmitted, an R filter 689d through which the red light R is transmitted, a W filter 689e through which the white light is transmitted.

The filter switching unit 678 switches the position of the rotation filter 677 to the light path of the broadband light source 676 in accordance with a control signal input by the control unit 52 and in accordance with the observation modes. Additionally, the filter switching unit 678 also adjusts the rotating speed of the rotation filter 677 in accordance with the observation modes. In the case of the normal observation mode, the filter switching unit 678 disposes the inner filter 688 on the light path of the broadband light source 676, and rotates the rotation filter 677 in accordance with to the imaging frames. The Bc image can be obtained in an imaging frame in which the BS filter 688a passes through the light path of the broadband light source 676. Similarly, the Gc image can be obtained in an imaging frame in which the G filter 688b passes through the light path of the broadband light source 676, and the Rc image can be obtained in an imaging frame in which the R filter 688c passes through the light path of the broadband light source 676.

Meanwhile, in the case of the special observation mode, the filter switching unit 678 disposes the outer filter 689 on the light path of the broadband light source 676, and rotates the rotation filter 677 in accordance with to the imaging frames. Accordingly, in the correction mode, in the respective imaging frames in which the respective filters 689a to 689e of the outer filter 689 pass the light path of the broadband light source 676, the Bp image, the Bq image, the Gr image, the Rs image, and the white light images 202 can be obtained. Additionally, in the oxygen saturation observation mode, the B1 image, the B2 image, the G2 image, and the R2 image can be obtained, respectively, in the respective imaging frames in which the BS filter 689a, the BL filter 689b, the R filter 689c, and the R filter 689d of the outer filter 689 pass through the light path of the broadband light source 676.

The above configuration of the rotation filter 677 is an example. For example, in a case where the compartment for the W filter 689e of the outer filter 689 is increased, and W filters 689e are also respectively disposed between the BS filter 689a and the BL filter 689b, between the BL filter 689b and the G filter 689c, and between the G filter 689c and the R filter 689d, the white light images 202 can be obtained in imaging frames during, before, or after the respective correction images, similarly to the first embodiment, in the correction mode. In addition, in a case where the image generation unit 73 generates the white light images 202 from the Bq image, the Gr image, and the Rs image, the W filter 689e may also be omitted. Additionally, the outer filter 689 may be further divided at the inner and outer peripheries, and a portion for the correction mode and a portion for the oxygen saturation observation modes may be provided.

Figure 27:
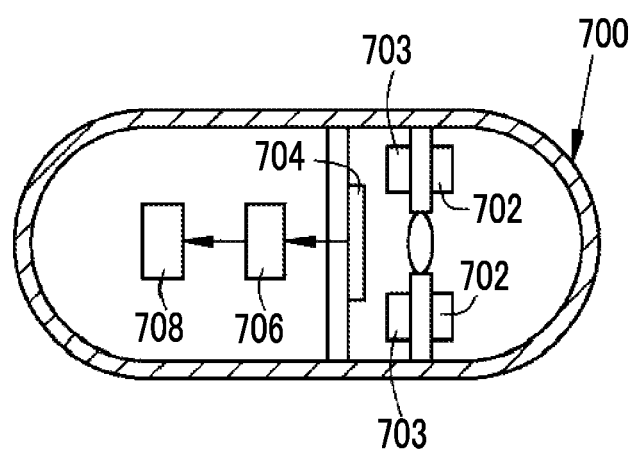
FIG. 27 is a schematic view of a capsule endoscope.

In addition, in the above first to fifth embodiments, the invention is carried out in the endoscope system that performs observation by inserting the endoscope 12 provided with the image sensor 48 into a subject. However, the invention is also suitable for a capsule endoscope system. As illustrated in FIG. 27, for example, the capsule endoscope system has at least a capsule endoscope 700 and a processor device (not illustrated).

The capsule endoscope 700 includes a light source unit 702, a control unit 703, an image sensor 704, an image processing unit 706, and a transmission/reception antenna 708. The light source unit 702 corresponds to the light source unit 20. The control unit 703 functions similarly to the light source control unit 22 and the control unit 52. Additionally, the control unit 703 is capable of wirelessly communicating with the processor device of the capsule endoscope system using the transmission/reception antenna 708. Although the processor device of the capsule endoscope system is substantially the same as that of the above processor device 16 of the first to fifth embodiments, the image processing unit 706 corresponding to the image acquisition unit 54 and the image processing unit 61 is provided in the capsule endoscope 700, and a generated oxygen saturation image or the like is transmitted to the processor device via the transmission/reception antenna 708. The image sensor 704 is configured similarly to the image sensor 48.

EXPLANATION OF REFERENCES 10, 670: endoscope system
12: endoscope
12a: insertion part
12b: operating part
12c: bending part
12d: distal end part
12e: angle knob
13a: switch
13b: zooming operation part
14: light source device
16: processor device
18: monitor
19: console
20, 702: light source unit
20a: BS light source
20b: BL light source
20c: G light source
20d: R light source
22: light source control unit
30a: illumination optical system
30b: imaging optical system
41: light guide
45: illumination lens
46: objective lens
47: zoom lens
48, 704: image sensor
52, 703: control unit
54: image acquisition unit
56: DSP
58: noise reduction unit
59: converting unit
61, 706: image processing unit
62: normal processing unit
63: special processing unit
66: display control unit
70: arithmetic value calculation unit
71: data storage unit
72: biological information calculation unit
73: image generation unit
75: correction information calculation unit
76: compensation amount calculation unit
77: correction unit
83: isoplethic line
84: isoplethic line
86, 87: graph
94: referential equal concentration line
96: equal concentration line
201: region setting unit
202: white light image
203: use region
301, 511, 611: movement amount calculation unit
302: positional deviation compensation unit
401, 521: light quantity ratio calculation unit
402: light quantity ratio compensation unit
612: determination unit
621: mucous membrane determination unit
676: broadband light source
677: rotation filter
678: filter switching unit
688, 689: band limiting filter
688a, 689a: BS filter
688b, 689c: G filter
688c, 689d: R filter
689b: BL filter
689e: W filter
700: capsule endoscope
708: transmission/reception antenna

What is claimed is:

1. An endoscope system having a biological information observation mode in which biological information on an observation object is observed, and a correction mode in which the biological information observation mode is corrected, the endoscope system comprising:
a light source unit that emits biological information observation illumination lights in the biological information observation mode and sequentially emits each of correction illumination lights in the correction mode and emits white light at least once in the correction mode, wherein the biological information observation illumination lights and the correction illumination lights are different from each other;
a processor, configured to:
acquire a plurality of correction images obtained by imaging the observation object using the correction illumination lights and acquire the plurality of white light images;
calculate a plurality of compensation amounts by using some correction images among the plurality of correction images and changing a combination of the correction images to be used;
calculate a movement amount of the observation object;

compensate for the data to be used in the biological information observation mode using a value obtained by weighting and averaging the plurality of compensation amounts using the movement amount;
correct a correlation to be used in the biological information observation mode using the plurality of compensation amounts;
calculate the biological information by imaging the observation object using the biological information observation illumination lights according to the corrected correlation; and
display a white light image, which is obtained by imaging the observation object using the white light, on a display unit in the correction mode.

2. The endoscope system according to claim 1, wherein the biological information is an oxygen saturation of the observation object.

3. The endoscope system according to claim 1, wherein the processor sets a portion of each of the correction images to a region to be used for the correction of the biological information observation mode,
wherein the processor overlappingly displays the region set on the white light mage.

4. The endoscope system according to claim 2, wherein the processor sets a portion of each of the correction images to a region to be used for the correction of the biological information observation mode,
wherein the processor overlappingly displays the region set on the white light image.

5. The endoscope system according to claim 2,
wherein in the connection mode, the plurality of correction images are acquired, and a plurality of the white light images are acquired.

6. The endoscope system according to claim 3,
wherein in the correction mode, the plurality of correction images are acquired, and a plurality of the white light images are acquired.

7. The endoscope system according to claim 1,
wherein the processor calculates a light quantity ratio of the plurality of white light images; and
wherein the processor compensates for a light quantity ratio of the plurality of correction images using the light quantity ratio.

8. The endoscope system according to claim 5,
wherein the processor calculates a light quantity ratio of the plurality of white light images; and
wherein the processor compensates for a light quantity ratio of the plurality of correction images using the light quantity ratio.

9. The endoscope system according to claim 6,
wherein the processor calculates a light quantity ratio of the plurality of white light images; and
wherein the processor compensates for a light quantity ratio of the plurality of correction images using the light quantity ratio.

10. The endoscope system according to claim 1,
wherein the processor calculates a movement amount of the observation object; and
wherein the processor compensates a positional deviation of the plurality of correction images using the movement amount.

11. The endoscope system according to claim 5,
wherein the processor calculates a movement amount of the observation object; and
wherein the processor compensates a positional deviation of the plurality of correction images using the movement amount.

12. The endoscope system according to claim 6,
wherein the processor calculates a movement amount of the observation object; and
wherein the processor compensates a positional deviation of the plurality of correction images using the movement amount.

13. The endoscope system according to claim 5,
wherein the processor calculates a plurality of the compensation amounts by using some correction images among the plurality of correction images and changing a combination of the correction images to be used, and
wherein the processor compensates for the data to be used in the biological information observation mode using the plurality of compensation amounts or one of the plurality of compensation amounts.

14. The endoscope system according to claim 6,
wherein the processor calculates a plurality of the compensation amounts by using some correction images among the plurality of correction images and changing a combination of the correction images to be used, and
wherein the processor compensates for the data to be used in the biological information observation mode using the plurality of compensation amounts or one of the plurality of compensation amounts.

15. The endoscope system according to claim 1,
wherein the light source unit includes a first blue light source, a green light source, a red light source, and a second blue light source that is narrower band than the first blue light source,
wherein the white light is a light configured to be turned on simultaneously by the first blue light source, the green light source, and the red light source,
wherein the correction illumination lights are lights configured to be turned on by the first blue light source, the second blue light source, the green light source, and the red light source with different timings,
wherein a light emission interval of a first blue light which is emitted by the first blue light source and a second blue light which is emitted by the second blue light source is shorter than a light emission interval of the other correction illumination lights.

16. A method of operating an endoscope system in claim 1 having a biological information observation mode in which biological information on an observation object is calculated, and a correction mode in which the biological information observation mode is corrected, the method comprising:
emitting biological information observation illumination lights in the biological information observation mode and sequentially emits each of correction illumination lights in the correction mode and emits white light at least once in the correction mode, wherein the biological information observation illumination lights and the correction illumination lights are different from each other;
acquiring a plurality of correction images obtained by imaging the observation object using the correction illumination lights and acquiring the plurality of white light images;
calculating a plurality of compensation amounts by using some correction images among the plurality of correction images and changing a combination of the correction images to be used;
calculating a movement amount of the observation object;
compensating for the data to be used in the biological information observation mode using a value obtained by weighting and averaging the plurality of compensation amounts using the movement amount;
correcting a correlation to be used in the biological in on ation observation mode using the plurality of compensation amounts;
calculating the biological information by imaging the observation object using the biological information observation illumination lights according to the corrected correlation; and
displaying a white light image, which is obtained by imaging the observation object using the white light, on a display unit in the correction mode.

* * * * *